United States Patent
Kanomata

(10) Patent No.: US 8,327,725 B2
(45) Date of Patent: Dec. 11, 2012

(54) SAMPLE COLLECTION CONTAINER, SAMPLE COLLECTION APPARATUS, AND SAMPLE COLLECTION METHOD IN SUPERCRITICAL FLUID SYSTEM

(75) Inventor: Takeshi Kanomata, Hachioji (JP)

(73) Assignee: JASCO Corporation, Hachioji-shi, Tokyo (JP)

( * ) Notice: Subject to any disclaimer, the term of this patent is extended or adjusted under 35 U.S.C. 154(b) by 550 days.

(21) Appl. No.: 12/567,743

(22) Filed: Sep. 26, 2009

(65) Prior Publication Data

US 2010/0077874 A1   Apr. 1, 2010

(30) Foreign Application Priority Data

Sep. 29, 2008 (JP) .................. 2008-249460

(51) Int. Cl.
*G01N 30/80* (2006.01)
*G01N 1/18* (2006.01)
*B01D 15/24* (2006.01)
*B01D 45/16* (2006.01)
*B01D 15/40* (2006.01)

(52) U.S. Cl. ............... 73/864.51; 73/61.55; 73/863.21; 73/863.24; 73/863.31; 73/863.32; 422/512; 422/550; 422/568; 422/546

(58) Field of Classification Search .......... 73/61.55, 73/863.21, 863.31–863.32, 864.24–864.25, 73/864.51; 422/512, 544–546, 549–550, 422/568, 570, 913–914, 916

See application file for complete search history.

(56) References Cited

U.S. PATENT DOCUMENTS

| 3,771,295 | A | | 11/1973 | Wheeler, Jr. | |
| 3,813,223 | A | * | 5/1974 | Fleck | 422/550 |
| 6,413,428 | B1 | | 7/2002 | Berger et al. | |
| 6,506,343 | B1 | * | 1/2003 | Bodner et al. | 422/65 |

(Continued)

FOREIGN PATENT DOCUMENTS

CA    2189879    1/1996

(Continued)

OTHER PUBLICATIONS

Japanese Patent Abstract for Publication No. 2007-120972 and machine translation of document published May 17, 2007, 32 pages.

(Continued)

*Primary Examiner* — Thomas P Noland
(74) *Attorney, Agent, or Firm* — Rankin, Hill & Clark LLP

(57) ABSTRACT

There is provided a sample collection container, a sample collection apparatus, and a sample collection method used in a supercritical fluid system capable of collecting a multi-constituent sample contained in a supercritical fluid at low cost and high collection efficiency. The pressure of a supercritical fluid containing a sample is reduced to a pressure close to the atmospheric pressure, and the depressurized supercritical fluid is forced to undergo adiabatic expansion to form gas-phase $CO_2$ containing a liquid component in the form of aerosol. The gas-phase $CO_2$ is fractionated for each constituent of the contained sample, transferred to a probe 60 of Liquid Handler, and dispensed into a large number of collection vials 300 under the atmospheric pressure, each of which is provided with a vial cap 100. The aerosol-containing gas-phase $CO_2$ is sprayed through the tip of an introduction tube 210 provided in each of the vial cap 100 in a direction downwardly-inclined from the tangential direction along an inner circumferential surface 308 of the corresponding collection vial 300, and swirls and falls in the collection vial 300. In this process, the liquid component containing the sample collides with the inner circumferential surface 308 and is trapped thereon, whereas the gas-phase $CO_2$ is discharged out of a discharge hole 109 in the vial cap 100.

18 Claims, 19 Drawing Sheets

U.S. PATENT DOCUMENTS

| | | | |
|---|---|---|---|
| 2002/0070169 A1 | 6/2002 | Berger et al. | |
| 2002/0070170 A1 | 6/2002 | Berger et al. | |
| 2002/0139752 A1 | 10/2002 | Berger et al. | |
| 2002/0144949 A1 | 10/2002 | Berger et al. | |
| 2003/0019812 A1 | 1/2003 | Berger et al. | |
| 2004/0180449 A1 | 9/2004 | Hamstra et al. | |
| 2006/0108285 A1 | 5/2006 | Bounoshita et al. | |
| 2007/0107539 A1* | 5/2007 | Bell et al. | 73/863.21 |
| 2011/0315011 A1* | 12/2011 | Black et al. | 95/79 |

FOREIGN PATENT DOCUMENTS

| | | | |
|---|---|---|---|
| DE | 19509732 A1 * | 11/1995 | |
| EP | 1380329 | 1/2004 | |
| JP | 2002-71534 | 3/2002 | |
| JP | 2006-136838 | 6/2006 | |
| JP | 2007-120972 | 5/2007 | |
| WO | 96/00369 | 1/1996 | |
| WO | WO 9826859 A1 * | 6/1998 | |
| WO | WO 03081212 A2 * | 10/2003 | |
| WO | 2008/011416 | 1/2008 | |

OTHER PUBLICATIONS

European Search Report for Application No. 09171172 mailed Feb. 26, 2010, five pages.

* cited by examiner (A)

(B)

(A)

(B)

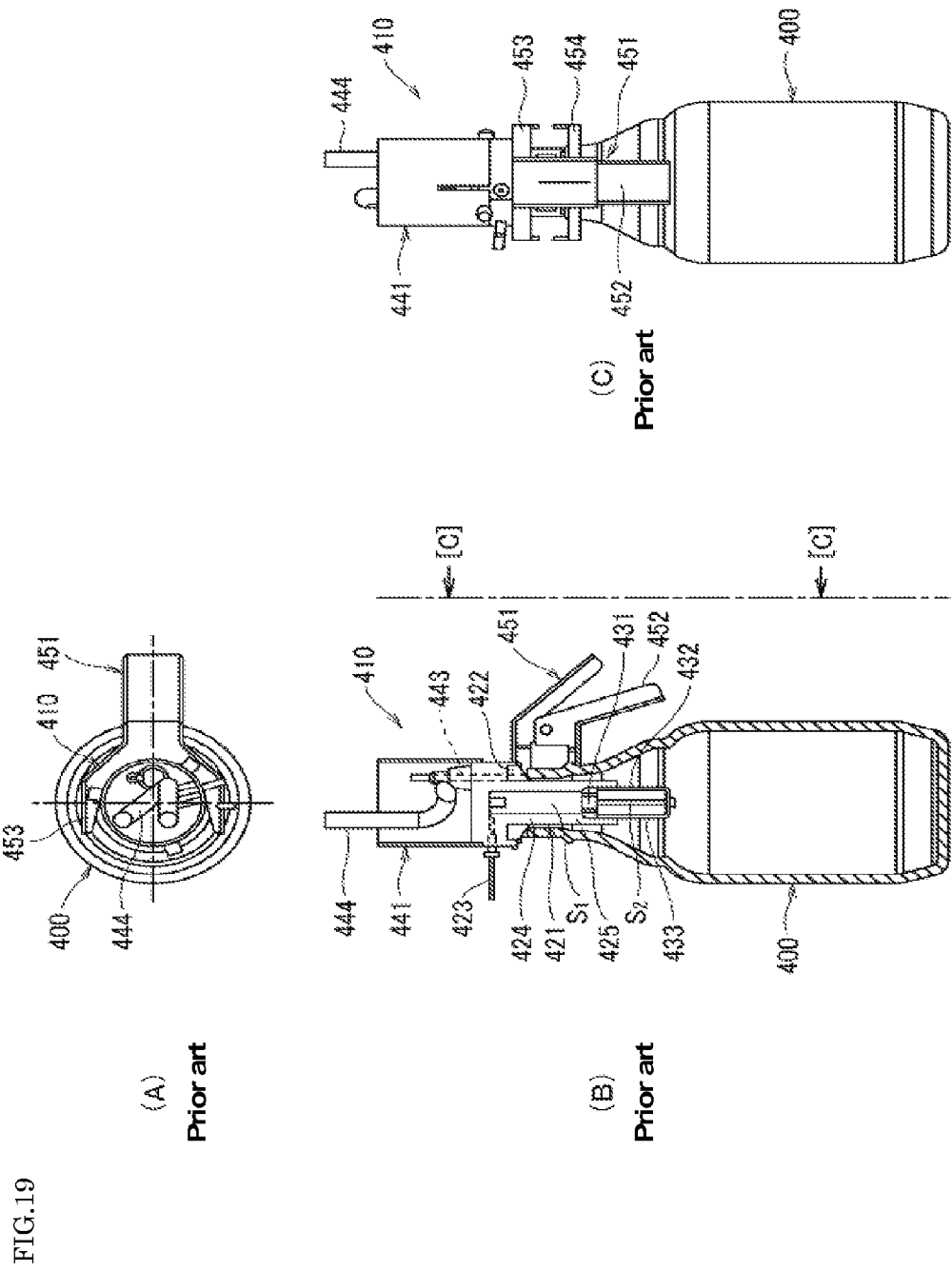

SAMPLE COLLECTION CONTAINER, SAMPLE COLLECTION APPARATUS, AND SAMPLE COLLECTION METHOD IN SUPERCRITICAL FLUID SYSTEM

RELATED APPLICATIONS

This application claims the priority of Japanese Patent Application No. 2008-249460 filed on Sep. 29, 2008, which is incorporated herein by reference.

FIELD OF THE INVENTION

The present invention relates to an improved sample collection container, a sample collection apparatus including the sample collection container, and a sample collection method using the sample collection container in a supercritical fluid system.

BACKGROUND OF THE INVENTION

In recent years, some industries have actively been using supercritical fluid chromatography (SFC), supercritical fluid extraction (SFE), or any other supercritical fluid system. The reason for this is that the solubility of a supercritical fluid can be changed by changing it's pressure and temperature. Among the materials used as the supercritical fluid, carbon dioxide ($CO_2$) is frequently used as the supercritical fluid in analysis and preparative usage, because $CO_2$ is advantageous not only in that it can be transferred to a supercritical fluid under relatively mild conditions, that is, at a critical temperature of 31.1° C. and a critical pressure of 7.38 MPa, but also in that $CO_2$ is chemically inert and highly pure $CO_2$ is available at low cost. To increase the degree of freedom of the separation mode in the analysis or preparative application, $CO_2$ mixed with organic solvents is also widely used. The organic solvents are also called a modifier. The modifier is added to liquid-phase $CO_2$ at a rate of approximately 50% at the maximum.

Japanese Patent Laid-Open No. 2002-71534 discloses a sample collection method used in any of the supercritical fluid systems described above which involves discharging a supercritical fluid containing a sample separated and eluted in a column (a mixed fluid of liquid-phase $CO_2$ and organic solvents) through an automatic back pressure regulator, transferring the supercritical fluid through a multi-port distribution value to a large number of corresponding transfer tubes, and loaded the supercritical fluid from the transfer tubes into bottles in a collection chamber maintained at a predetermined pressure (20 to 100 psi≈0.14 to 0.69 MPa). In this process, to prevent the $CO_2$ from abruptly evaporating and the organic solvents from becoming an aerosol and scattering, the transfer tubes are heated and the collection chamber and the bottles are maintained under the pressure described above. There is a possibility that flow path is cooled by endoergic reaction owing to adiabatic expansion of $CO_2$, and thus the sample tends to be a solid. In order to inhibit plugging the tubes and the chamber with the solid, they are heated. The Gas-liquid-phase fluid is spirally delivered into the bottles. The gas-phase $CO_2$ is discharged from the bottles under a predetermined pressure, and the liquid-phase organic solvents are collected in the bottles.

Japanese Patent Laid-Open No. 2007-120972 discloses a sample collection apparatus in a supercritical fluid system for collecting a multi-constituent sample injected into a mixed fluid of liquid-phase $CO_2$ and a modifier. The apparatus involves separating the sample in a column for each of the constituents, reducing the pressure of the supercritical fluid containing each of the eluted samples in an automatic back pressure regulator to a pressure close to the atmospheric pressure, fractionating the gas containing the thereby formed aerosol through a flow path distribution valve, delivering each of the fractionated gases through the corresponding line to the corresponding Gas-liquid separator to separate the gas-phase $CO_2$ and spirally spray the liquid component containing the sample in the Gas-liquid separator to form droplets, and causing the droplets to fall into a collection bottle connected to the Gas-liquid separator. That is, the gas-phase $CO_2$ and the liquid component are separated from each other in the slightly pressurized Gas-liquid separator.

In addition to the Gas-liquid separator disclosed in Japanese Patent Laid-Open No. 2007-120972, there is a cap-type Gas-liquid separator 410, which is attached, when used, to an upper-end opening of a collection container 400, as shown in FIGS. 19A to 19C. That is, FIG. 19A is a plan view of the collection container 400 to which the cap-type Gas-liquid separator 410 is attached. FIG. 19B is a longitudinal cross-sectional view of the assembled structure. FIG. 19C is a side view of the assembled structure viewed in the direction indicated by the line [C]-[C] in FIG. 19B. As shown in FIG. 19B, the Gas-liquid separator 410 includes a Gas-liquid separating unit 421 most of which is inserted into the collection container 400, an exhausting gas unit 441 provided on the Gas-liquid separating unit 421, and a clipping unit 451 used to attach the Gas-liquid separator 410 to the collection container 400.

The Gas-liquid separating unit 421 is as a whole placed on the upper end of the collection container 400 and fixed thereto by a seat 422. An introduction line 423 for introducing a gas containing a fractionated aerosol is provided on a side of an upper end portion of the Gas-liquid separating unit 421 so that the gas flows into a cylindrical space $S_1$, which will be described later, in a tangential direction. A heater 424 having the cylindrical space $S_1$ is provided downstream of the introduction line 423. A sintered stainless filter 432 having a cylindrical shape with a bottom is fixed to the lower end of the heater 424 by a fixing buffer plate 431 and hanged therefrom. The structure described above forms a separating unit 433. A space $S_2$ surrounded by the sintered filter 432 connects with the space $S_1$ in the heater 424.

In the exhausting gas unit 441, a discharge duct 443 is connected to the upper end of the space $S_1$ in the heater 424, and a discharge duct 444 is connected to the discharge duct 443. An upper clipping part 453 of the clipping unit 451 is attached to an upper end portion of the Gas-liquid separating unit 421, and the Gas-liquid separator 410 is attached and detached to and from the collection container 400 via an openable lower clipping part 454 that grips the neck of the collection container 400. The lower clipping part 454 is opened and closed by operating a movable lever 452 of the clipping unit 451.

The gas containing a liquid component aerosol introduced through the introduction line 423, after moved from the space $S_1$ in the heater 424 to the space $S_2$ in the separating unit 433, is discharged through the sintered stainless filter 432 into the collection container 400 in all directions, whereby the linear velocity of the fluid is significantly reduced. As a result, the adhesion between the liquid component and the sintered stainless filter 432 is greater than the force that causes the liquid component passing through the micro pore in the sintered stainless filter 432 to scatter, whereby the scattering of the liquid component will be suppressed. The liquid component moves downward due to the gravity and drops through the bottom of the sintered stainless filter 432 into the collection container 400.

DISCLOSURE OF THE INVENTION

Problem to be Solved by the Invention

The sample collection method used in a supercritical fluid system described in Japanese Patent Laid-Open No. 2002-71534 is disadvantageous in cost of the increased apparatus because the bottles for collecting the sample are kept being pressurized. Further, since a multi-port distribution valve is used, the number of ports disadvantageously limits the number of sample constituents that can be separated. The supercritical fluid system illustrated in Japanese Patent Laid-Open No. 2007-120972 also not only uses a multi-port flow path distribution value but also requires Gas-liquid separators. That is, both in Japanese Patent Laid-Open Nos. 2002-71534 and 2007-120972, when the number of sample constituents increases, the multi-port distribution valve needs to have ports corresponding to the number of sample constituents. The larger the number of ports, the more expensive the multi-port distribution valve is. When no multi-port distribution valve with the necessary number of ports is commercially available, multiple multi-port distribution valves are used, resulting in complicated control.

A supercritical chromatography apparatus that includes a sample collection apparatus with Gas-liquid separators and uses a mixed fluid of liquid-phase $CO_2$ and a modifier as a supercritical fluid will be described as an example of related art before the present invention is described. FIG. 1 is a schematic view showing a typical configuration of such an apparatus.

In a supercritical fluid chromatographic apparatus 1 shown in FIG. 1, liquid-phase $CO_2$ supplied from a $CO_2$ cylinder 11 into a line is delivered to a heat exchanger in a $CO_2$ pump 13 and cooled down to $-10°$ C. by the heat exchanger to completely turn to liquid-phase $CO_2$. The thus sufficiently cooled liquid-phase $CO_2$ is pumped through a pumping head of the $CO_2$ pump 13 at a high pressure.

On the other hand, a modifier pump 14 delivers a modifier supplied from a modifier container 12 into the pumped liquid-phase $CO_2$, and the modifier is mixed with the liquid-phase $CO_2$. The mixed fluid, which is a supercritical fluid, is heated by a pre-heating coil 15 to a temperature suitable for separation in a column 19, which will be described later, and then delivered to a loop-injection-type injector 16. After a syringe pump 17 delivers a sample to the loop, the sample is injected to the column 19 by switching the injector 16.

The sample having been injected into the mixed fluid and dissolved therein is loaded in the column 19 in a column oven 18 and separated into each constituent of the sample. Each of the sample constituents contained in the mixed fluid eluted from the column 19 is monitored by a detector 20 responding to any of the characteristics of the sample (optical absorbance, for example), and then reaches an automatic back pressure regulator 21. The pressure of the mixed fluid from the $CO_2$ pump 13 and the modifier pump 14 to the automatic back pressure regulator 21 is adjusted to a predetermined value by the automatic back pressure regulator 21.

The pressure of the mixed fluid ranges from approximately 10 to 35 MPa on the side upstream of the automatic back pressure regulator 21, and becomes approximately normal pressure on the side downstream of the automatic back pressure regulator 21. Therefore, the liquid-phase $CO_2$ undergoes adiabatic expansion and evaporates, and the temperature thereof decreases. At this point, the sample is dissolved in the liquid component primarily formed of the modifier. The rapidly expanding gas-phase $CO_2$ aerosolizes the liquid component, which is then transferred through the line.

After heated by a pre-heater 22, the gas containing the aerosol in which no sample is dissolved is discharged out of the system through a flow path switching valve 23. The gas containing the aerosol in which the sample is dissolved is transferred from the flow path switching valve 23, which is switched controlled under a signal from the detector 20, through a line 24 to an eight-direction distribution valve 25, and then delivered via an introduction line 26 corresponding to the dissolved sample to a Gas-liquid separator 27.

In the Gas-liquid separator 27, the gas-phase $CO_2$ is separated and discharged out of the system, and the liquid component is trapped in the Gas-liquid separator 27 when it spirally swirls therein. During the swirling, the trapped liquid component grows into droplets, which drop into a collection container 28 connected to the lower end of the Gas-liquid separator 27, and are collected in the collection container 28. The entire system is controlled by a computer 38.

The rapid changes in temperature and pressure described in the paragraph [0015] tend to cause the following troubles:

(1) When the $CO_2$ undergoes the adiabatic expansion and hence the temperature thereof decreases, the modifier sometimes solidifies in addition to formation of dry ice which is solidified $CO_2$. In this case, the introduction line 26 to the collection container 28 tends to be clogged.

(2) When the $CO_2$ undergoes the adiabatic expansion, not only does the liquid component scatter but also the flow rate of the gas-phase $CO_2$ increases particularly at the outlet of the introduction line 26 and hence the flow speed highly increases. Therefore, most of the accompanying liquid component can not be stayed and kept in the collection container 28, resulting in collection loss.

(3) When the introduction line 26 starts to be clogged, the pressure increases. Therefore, the high pressure eliminates the clogging, but the flow speed of the gas-phase $CO_2$ further increases immediately after the clogging is eliminated. The increased flow speed lets the liquid component scatter more, and hence the collection efficiency of the sample decreases.

(4) When the dry ice or the solidified modifier is accumulated in the collection container 28, the dropping droplets of the modifier overflow the collection container 28.

When a supercritical fluid is used to separate a sample and collect it, the troubles described above cannot be eliminated or the sample cannot be collected in a satisfactory manner only by using a typical fraction collector in high-performance liquid chromatography (HPLC) and guiding the fraction collector line to the collection container 28. That is, a variety of types of fraction collectors used in high-performance liquid chromatography are commercially available, but any of the fraction collectors uses a test tube or a flask to receive droplets that drop by gravitation through the line. Using such a fraction collectors in a supercritical fluid chromatography apparatus or a supercritical fluid extraction apparatus in which gas-phase $CO_2$ containing a liquid component aerosol is sprayed hardly allows the liquid component to be collected.

Further, the supercritical fluid chromatographic apparatus 1 of related art shown in FIG. 1 is configured in such a way that the gas containing the fractionated aerosol travels through the introduction line 26 connected to any of the ports of the eight-direction distribution valve 25 and the Gas-liquid separator 27 and is then collected in the collection container 28. While the number of ports in the above description is eight, the number of ports of a multi-port distribution valve in general is approximately ten at the maximum, as described above. When the number of constituents in a sample is greater than the number of ports, all the sample constituents cannot be collected. To overcome the problem, it is conceivable to incorporate multiple multi-port distribution valves in the apparatus, but the fact that a multi-port distribution valve is expensive results in an expensive apparatus.

Means to Solve the Problem

The present invention has been made in view of the above problems, and a first object of the present invention is to provide a sample collection container capable of collecting a large number of constituents contained in a sample at low cost and high collection efficiency in a supercritical fluid system.

A second object of the present invention is to provide a sample collection apparatus including the sample collection container and a sample collection method using the sample collection container.

To achieve the objects of the present invention, a sample collection container according to claim 1 used in a supercritical fluid system comprises a cylindrical collection vial into which an aerosol-containing gas formed by reducing the pressure of a supercritical fluid containing a sample eluted in a separating unit to a pressure close to the atmospheric pressure is loaded to collect the sample, and a vial cap attached to an upper end opening of the collection vial. The vial cap includes a discharge hole through which the collection vial connects with the outer air and an introduction path through which the aerosol-containing gas is externally introduced into the collection vial. A distal end portion of the introduction path has an opening in the vicinity of the inner circumferential surface of the collection vial, and the opening is oriented in the tangential direction of the inner circumferential surface or in a direction downwardly-inclined from the tangential direction. The aerosol-containing gas is injected under the atmospheric pressure.

The sample collection container described above is used to dispense a gas containing a liquid component in the form of aerosol through the introduction path in the vial cap into the collection vial. Since the distal end portion of the introduction path is positioned in the vicinity of the inner circumferential surface of the collection vial and the opening of the distal end portion is oriented in the tangential direction of the inner circumferential surface or a direction inclined downward from the tangential direction, the aerosol-containing gas sprayed out of the distal end portion flows along the inner circumferential surface of the collection vial while swirling therealong. The cylindrical collection vial therefore serves as a cyclone separator. That is, the gas exits through the discharge hole in the vial cap into the outer air, whereas the liquid component in the form of aerosol collides with the inner circumferential surface of the collection vial and is trapped thereon. The trapped liquid component then grows into droplets, the diameter of which increases due to successive aerosol collision, and the droplets move downward and are collected at the bottom of the collection vial.

The sample collection container according claim 2 is the sample collection container according claim 1, wherein the introduction path is formed of an introduction hole vertically drilled in the vial cap and an introduction tube connected to the introduction hole.

In the sample collection container described above, the introduction tube can be designed properly, resizing of internal diameter of tube, length of tube and/or injection direction of tube in accordance with the flow rate of the supercritical fluid and the properties of the sample.

The sample collection container according claim 3 is the sample collection container according claim 2, wherein the introduction tube includes a straight portion connected to the introduction hole and a spiral portion following the straight portion and extending along the inner circumferential surface of the collection vial.

In the sample collection container described above, the sample can be collected by causing the liquid component sprayed out of the tip of the spiral portion of the introduction tube to fall and swirl along the inner circumferential surface of the collection vial.

The sample collection container according claim 4 is the sample collection container according claim 2 or 3, wherein the distal end portion of the introduction tube attached to the vial cap is cut in a slanting direction.

In the sample collection container described above, a gas is smoothly separated from the aerosol-containing gas sprayed out of the opening of the distal end portion of the introduction tube.

The sample collection container according claim 5 is the sample collection container according claim 1, wherein the introduction path is formed of an introduction hole vertically drilled in the vial cap, a introduction hole drilled in a cylindrical extension extending from the vial cap into the collection vial, and a plurality of distribution holes extending from the introduction hole to the outer circumferential surface of the extension, each of the distribution holes having an opening at the outer circumferential surface.

In the sample collection container described above, since the introduction path itself does not vibrate and the aerosol-containing gas to be injected is distributed into the plurality of distribution holes, the speed at which the aerosol-containing gas is sprayed out through the opening of each of distribution holes is greatly reduced, whereby the sample can be collected in a stable manner.

The sample collection container according claim 6 is the sample collection container according claim 5, wherein each of the distribution holes has an arcuate shape, and horizontally extends from the lower end of the introduction hole or is inclined downward along a conical surface whose apex coincides with the lower end of the introduction hole.

The sample collection container described above can cause the aerosol-containing gas sprayed out of the opening of each of the distribution holes to fall and swirl along the inner circumferential surface of the collection vial. In this case, the collection vial serves as a cyclone separator, which increases the sample collection efficiency.

The sample collection container according claim 7 is the sample collection container according claim 1, wherein at least an upper portion of the vial cap is shaped into a truncated cone, and the outer circumferential surface of the upper portion is supported by the end of an upper end opening of the collection vial or a flange provided at the periphery of the vial cap is placed on the end of the upper end opening of the collection vial.

In the sample collection container described above, the vial cap supported by or placed on the upper end portion of the collection vial will not slide sideward, and the vial cap is very easily attached and detached to and from the collection vial.

A sample collection apparatus according to claim 8 is used in a supercritical fluid system in which a gas containing a liquid component in the form of aerosol formed by reducing the pressure of a supercritical fluid containing a sample eluted in a separating unit to a pressure close to the atmospheric pressure is fractionated and the gas containing the fractionated aerosol is dispensed into a sample collection containers, and the sample collection apparatus comprises a plurality of sample collection containers, each of which includes the cylindrical collection vial and the vial cap according to any of claims 1 to 7, and a probe that can be moved to a position above each of the collection vials, the probe lowered from the position above the collection vial and dispensing the gas containing the fractionated aerosol into the collection vial under the atmospheric pressure.

In the sample collection apparatus described above, when the pressure of the supercritical fluid in which the sample is dissolved is reduced to a pressure close to the atmospheric pressure, gas-phase $CO_2$ that undergoes adiabatic expansion causes the liquid component containing the sample to disperse and transfer the liquid component to a mist-like aerosol. The aerosol-containing gas is fractionated for each of the contained constituents. The gas containing the fractionated aerosol travels from a distal end portion of the probe to the introduction path in the vial cap. The gas containing the fractionated aerosol is then dispensed by spraying it along the inner circumferential surface of the cylindrical collection vial under atmospheric pressure. The collection vial is operated to serve as a cyclone separator, whereby the gas component is discharged through the discharge hole provided in the vial cap into the outer air. Therefore, the liquid component containing the sample can be efficiently collected in the collection vial.

A sample collection method according to claim 9 is used in a supercritical fluid system in which a gas containing a liquid component in the form of aerosol formed by reducing the pressure of a supercritical fluid containing a sample eluted in a separating unit to a pressure close to the atmospheric pressure is fractionated and the gas containing the fractionated aerosol is dispensed into a sample collection container, and the sample collection method uses a plurality of sample collection containers, each of which includes the cylindrical collection vial and the vial cap according to any of claims 1 to 7 and a probe that can be moved to a position above each of the collection vials, the probe lowered from the position above the collection vial and dispensing the gas containing the fractionated aerosol into the collection vial under the atmospheric pressure. The sample collection method comprises bringing a distal end portion of the probe lowered from above into fluid-leakage-free contact (i.e. intimate contact) with the introduction path in the vial cap, dispensing the gas containing the fractionated aerosol through an end opening of the introduction path into the collection vial, and collecting the liquid component containing the sample in the collection vial and discharging the gas out of the discharge hole in the vial cap into the outer air.

In the sample collection method described above, when the pressure of the supercritical fluid in which the sample is dissolved is reduced to a pressure close to the atmospheric pressure, gas-phase $CO_2$ that undergoes adiabatic expansion causes the liquid component containing the sample to disperse and transfer the liquid component to a mist-like aerosol. The aerosol-containing gas is fractionated for each of the contained constituents. The gas containing the fractionated aerosol travels from a distal end portion of the probe to the introduction path in the vial cap. The gas containing the fractionated aerosol is then dispensed by spraying it along the inner circumferential surface of the cylindrical collection vial under atmospheric pressure. The collection vial is operated to serve as a cyclone separator, whereby the gas component is discharged through the discharge hole provided in the vial cap into the outer air. Therefore, the liquid component containing the sample can be efficiently collected in the collection vial.

According to the sample collection container, the sample collection apparatus, and the sample collection method in the supercritical fluid system of the present invention, the sample collection container does not need to be pressure resistant but the vial cap and the collection vial can be made of resin, because the sample collection is performed under the atmospheric pressure. Therefore, typical thermal forming using a mold can be employed, and the vial cap and the collection vial can be manufactured at low cost. The collection vial can of course be made of glass.

Further, since the cylindrical collection vial is operated to serve as a cyclone separator, the separated gas, that did not contain the aerosol, rises in the collection vial and is removed out of the discharge hole in the vial cap, whereas the liquid component containing the sample in the form of aerosol collides with the inner circumferential surface of the collection vial and is trapped thereon, grows into droplets, the diameter of which increases due to successive aerosol collision, and moves to the bottom of the collection vial. The sample can therefore be collected in the collection vial at high collection efficiency.

Moreover, a multi-port distribution valve having a limited number of ports is not used, but a probe that can be moved to a position above each of a large number of collection vials is used to dispense an aerosol-containing gas into a vial cap of the collection vial. Therefore, even when the number of samples to be separated and fractionated is large, all the samples can be collected by preparing collection vials corresponding to the number of samples.

BRIEF DESCRIPTION OF THE DRAWINGS

FIGS. 19A to 19C show an example of a Gas-liquid separator.

BEST MODE FOR CARRYING OUT THE INVENTION

An improved sample collection container, a sample collection apparatus including the sample collection container, and a sample collection method using the sample collection container in a supercritical fluid system according to the present invention will be described with reference to the drawings.

<Sample Collection Apparatus>

Figure 1:
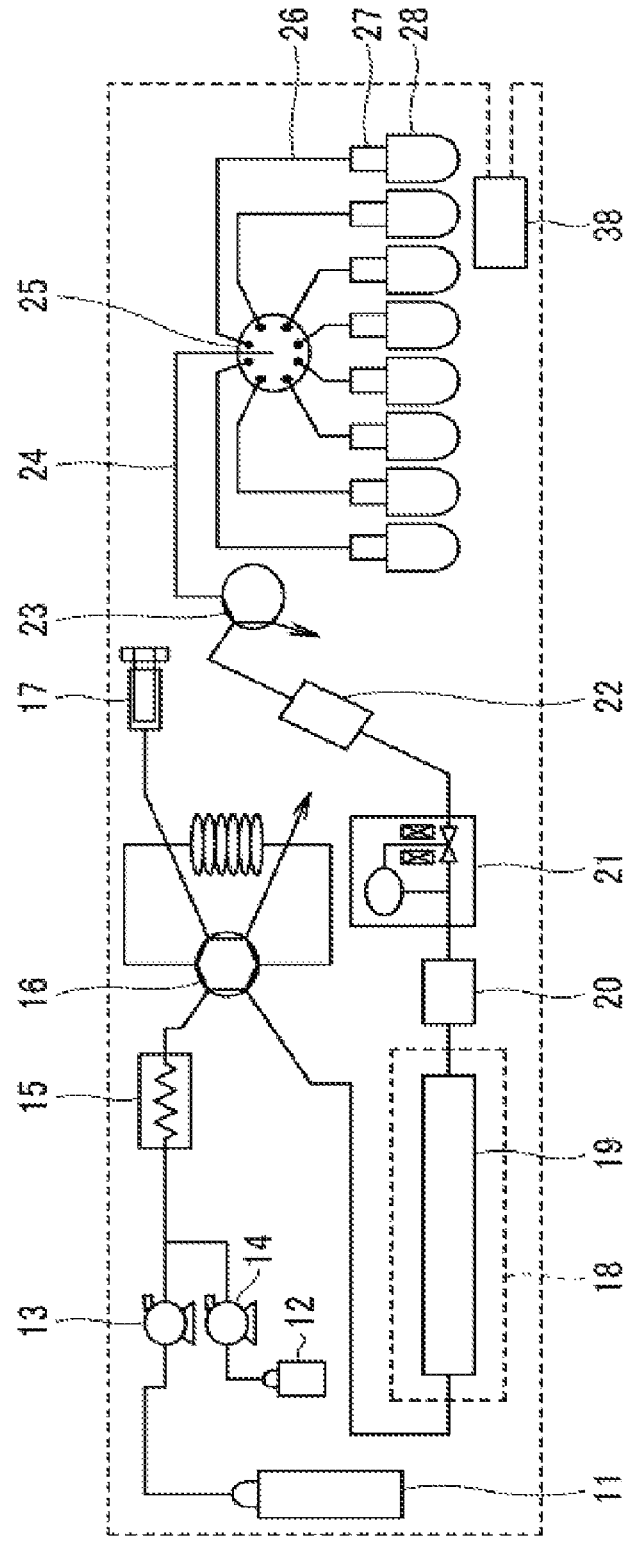
FIG. 1 is a schematic view showing the configuration of a typical supercritical fluid chromatographic apparatus 1 including a sample collection apparatus of prior art formed of collection bottles connected to Gas-liquid separators.
Figure 2:
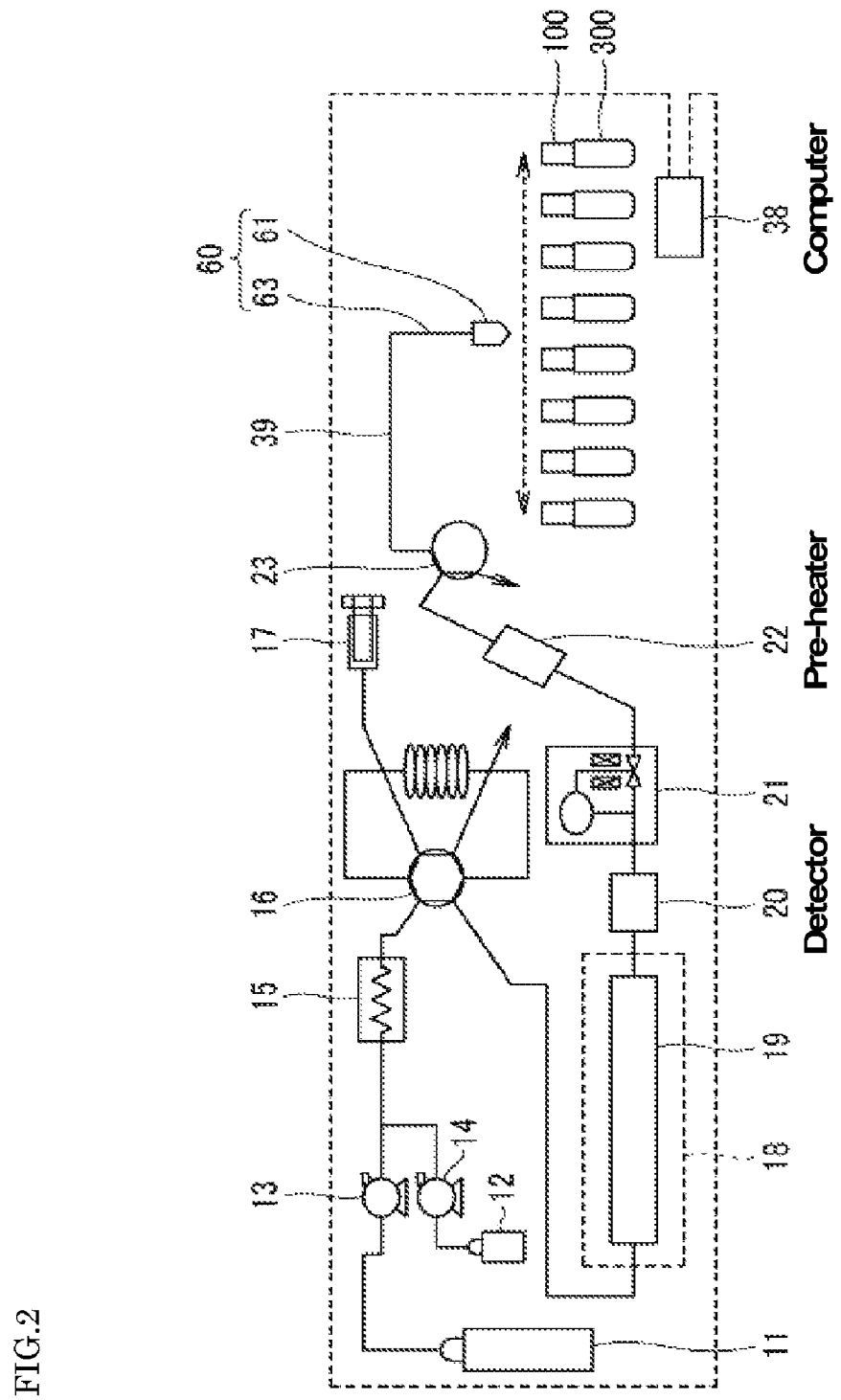
FIG. 2 schematically shows an overall configuration of a supercritical fluid chromatography apparatus 2 including a sample collection apparatus with sample collection containers of the present invention.

FIG. 2 shows the configuration of a supercritical fluid chromatographic apparatus 2 including a sample collection container of the present invention. FIG. 2 corresponds to FIG. 1 showing the supercritical fluid chromatographic apparatus 1 of related art. Among the components of the apparatus 2 shown in FIG. 2, the components that are the same as those of the apparatus 1 shown in FIG. 1 have the same reference characters and the description thereof will be omitted.

The supercritical fluid chromatographic apparatus 2 shown in FIG. 2 differs from the apparatus 1 shown in FIG. 1 in that the downstream side of the flow path switching valve 23 is connected to a flexible resin tube 39 followed by a stainless steel tube 63 of a probe 60 movable in three directions, X, Y, and Z, and an aerosol-containing gas is dispensed through a probe distal end portion 61 into a large number of collection vials 300, each of which is provided with a vial cap 100. That is, in the supercritical fluid chromatographic apparatus 2, no Gas-liquid separator 27 shown in FIG. 1 is provided upstream of each of the vial caps 100 and the collection vials 300. The entire apparatus 2 shown in FIG. 2 is controlled by a personal computer 38, as in the apparatus 1 shown in FIG. 1.

FIG. 3 is an overall perspective view showing a sample collection apparatus 40 that moves the probe 60 described above in the X, Y, and Z three directions and injects the aerosol-containing gas into a large number of collection vials 300 to collect a sample. In FIG. 3, an XYZ movement mechanism 41 that moves the probe 60 in the X, Y, and Z three directions includes a horizontal arm 52 which can be moved in the X direction by a movable X axis and a vertical arm 53 disposed on the horizontal arm 52 which can be moved in the Y direction by a movable Y axis. The stainless steel tube 63 is attached to the vertical arm 53 movably in the Z direction (up/down direction). The XYZ movement mechanism 41 is commercially available from Gilson, Inc. under the trade name "Liquid Handler."

In the sample collection apparatus 40, multiple vial racks 45 are arranged on a tray 44 fixed to a bottom plate 43 to which the XYZ movement mechanism 41 is fixed. The cylindrical collection vials 300 combined with the vial caps 100 shown, for example, in FIG. 7, which will be described later, are inserted into and held in a large number of holding holes 47 formed in a top plate 46 of each of the vial racks 45. While the above description has been made with reference to the "Liquid Handler," any other mechanism having a function similar to that of the "Liquid Handler" may be used.

FIGS. 4A and 4B show the vial racks 45. FIG. 4A is a plan view of four vial racks 45 and shows an example of how the holding holes 47 are arranged in the top plates 46. The numerals labeled in the holding holes 47 in the leftmost vial rack 45 represent an example of the order in which the aerosol-containing gas is dispensed. FIG. 4B is a perspective view of any one of the vial racks 45. The XYZ movement mechanism 41 moves the probe 60 relative to the collection vials 300 held in the holding holes 47. The probe 60 is formed of the stainless steel tube 63 to which the distal end portion 61 is attached and other components. A gas that contains a liquid component aerosol containing a sample is dispensed through the probe distal end portion 61.

FIG. 5 is an enlarged perspective view showing part of the probe 60 and the XYZ movement mechanism 41. As shown in FIG. 5, a guide groove 54 extending in the up/down direction is provided in a side surface of the vertical arm 53, and a slider 55 including an actuator (not shown) can be moved in the up/down direction (Z direction) along the guide groove 54. The stainless steel tube 63, which transfers the aerosol-containing gas, is attached to the slider 55. As described above, the downstream end of the flexible tube (resin tube, for example) 39 shown in FIG. 2 is connected to the upper end of the stainless steel tube 63 via a joint.

FIG. 6 is a partial cross-sectional view showing the entire probe 60. An upper end portion of the stainless steel tube 63 is held on slider 55 in such a way that the stainless steel tube 63 is slidable in the Z (up/down) direction. The lower half of the stainless steel tube 63 is surrounded by a guide pipe 64 for preventing the stainless steel tube 63 from being bent, and a bush 66 that slidably holds the stainless steel tube 63, which moves in the Z direction, is provided at each of the upper and lower ends of the guide pipe 64. The guide pipe 64 is fixed to the vertical arm 53 with a fixing member 67.

The probe distal end portion 61 for a dispensing operation is attached to the lower end of the stainless steel tube 63 via a joint 68. The tip of the probe distal end portion 61 has a hemispherical shape, and an injection hole 62 is drilled through the tip. When the probe 60 is lowered, the probe distal end portion 61 attaches to any of the vial caps 100.

FIG. 7 shows an example of the sample collection container of the present invention. The sample collection container shown in FIG. 7 is formed of any of the collection vial 300 combined with the vial cap 100 for dispensing the aerosol-containing gas into the collection vial 300 described above. The collection vial 300 is formed of a cylindrical body 301 and a wide-mouth neck 302. The outer circumferential surface of the vial cap 100, the diameter of which increases toward the upper end, is secured by the wide-mouth neck 302. The attachment and detachment of the vial cap 100 is therefore very readily carried out. While the collection vial 300 can be used with the vial cap 100 simply attached thereto, the collection vial 300 can also be used with a screw cap 304 (indicated by the dashed line in FIG. 7) having a central hole screwed to the collection vial 300 in order to more reliably fix the vial cap 100.

When the stainless steel tube 63 of the probe 60 is lowered, the probe distal end portion 61 comes into fluid-leakage-free contact with an inner wall 104 around an introduction hole 103 in the vial cap 100, and the injection hole 62 in the probe distal end portion 61 is connected to the introduction hole 103 in the vial cap 100, as shown in FIG. 7. The inner wall 104 of the lower half of the vial cap 100 is a conical surface except the portion where the introduction hole 103 is formed, as also will be shown in FIG. 8, which will be described later. Since the tip of the probe distal end portion 61 has a hemispherical shape, the probe distal end portion 61 comes into intimate contact with the inner wall 104 of the vial cap 100, and the injection hole 62 in the probe distal end portion 61 is connected to the introduction hole 103 in the vial cap 100 in such a way that the axes of the two holes are aligned with each other.

Figure 8:
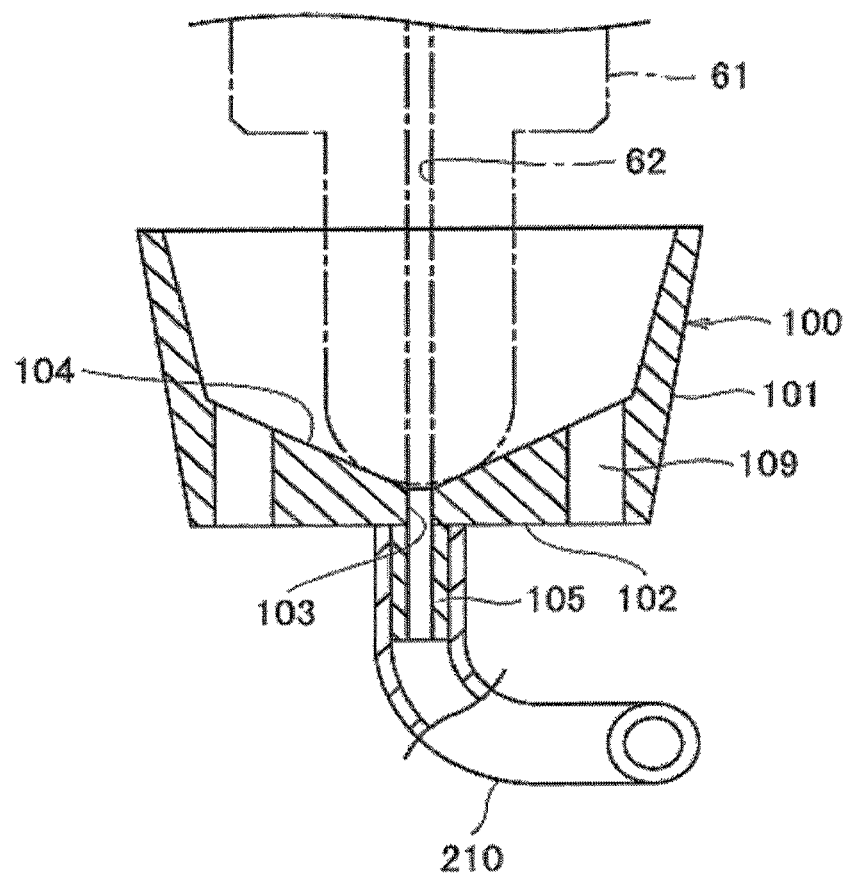
FIG. 8 is an enlarged cross-sectional view showing an example of the vial cap.

FIG. 8 is an enlarged cross-sectional view showing the vial cap 100. As shown in FIG. 8, a body 101 of the vial cap 100 has a cup-like shape, and the introduction hole 103 extending in the up/down direction is drilled in a central portion of a bottom portion 102 of the body 101. An attachment tube 105 protruding from the lower surface of the bottom portion 102 has a hollow hole the axis of which coincides with the axis of the introduction hole 103. An introduction tube 210 that introduces the aerosol-containing gas into the collection vial 300 is fitted in and fixed to the outer circumferential surface of the attachment tube 105.

Figure 7:
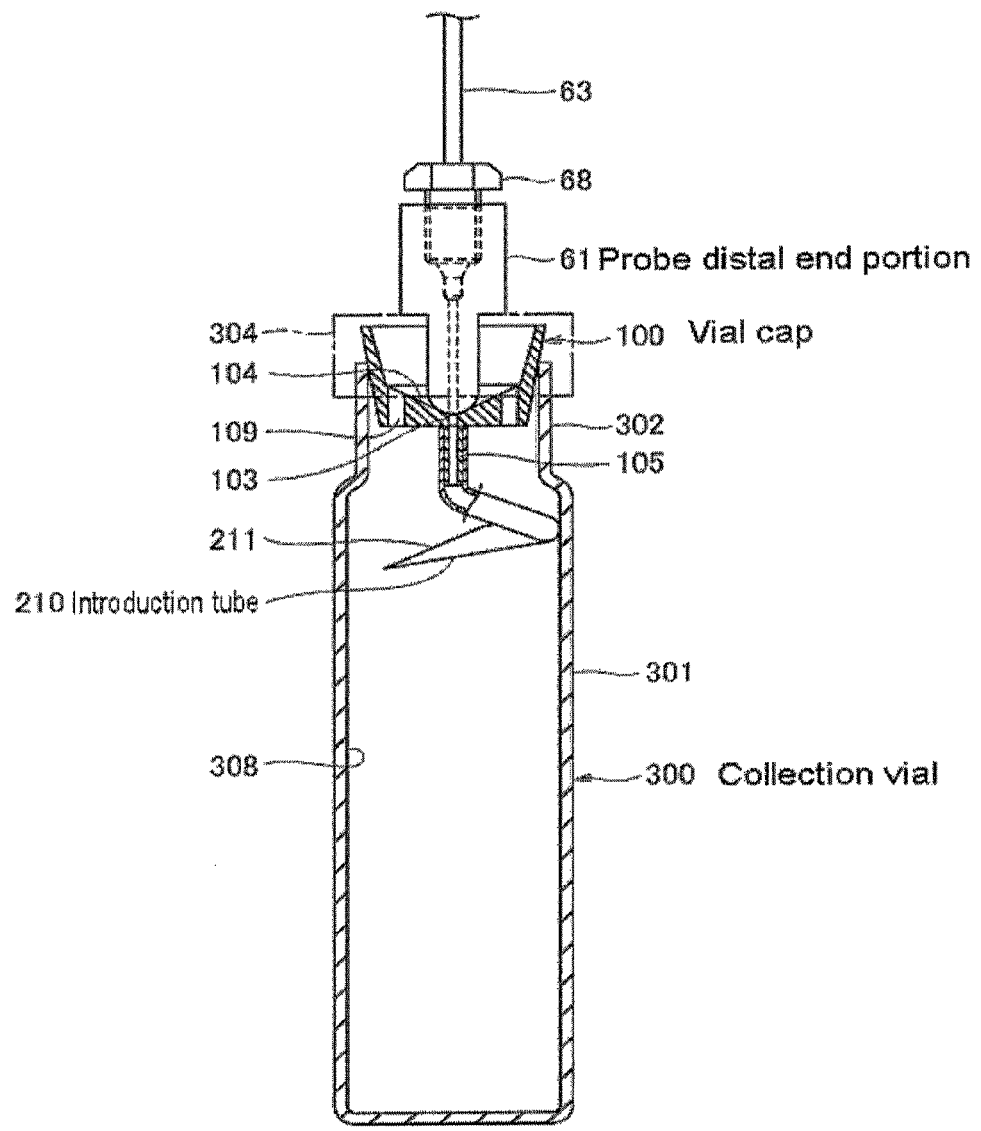
FIG. 7 is a cross-sectional view showing an example of a collection vial combined with a vial cap.

As shown in FIG. 7, the introduction tube 210 has an arcuate shape that comes into contact with an inner circumferential surface 308 of the collection vial 300, and is shorter in length than or equal to the circumferential length of the inner circumferential surface 308. Or, the introduction tube 210 does not always have to come into contact with the inner circumferential surface 308 as long as a distal end opening 211 of the introduction tube 210 is located near the inner circumferential surface 308. The tip of the introduction tube 210 is inclined downward from the horizontal tangential direction (inclined by an angle ranging from 5 to 20 degrees). The aerosol-containing gas is sprayed out of a distal end opening 211 of the introduction tube 210 along the inner circumferential surface 308 of the collection vial 300, and separated to gas-phase $CO_2$ and a liquid component. It has been found that cutting the tube on a slant and orienting the cut surface of the distal end opening 211 of the introduction tube 210 upward allow the gas-phase $CO_2$ to be separated in the most satisfactory manner. That is, it has been ascertained that the liquid component is not carried upward by the upward flow of gas phase $CO_2$ for a exhaust. The introduction tube 210 described above may be integrally formed with the body 101 of the vial cap 100 without using the attachment tube 105.

In addition to the components described above, discharge holes 109 extending from the lower surface of the bottom portion 102 to the inner wall 104 are formed in the vial cap body 101, as shown in FIGS. 7 and 8. The discharge holes 109 are used to remove the gas-phase $CO_2$ rising through the collection vial 300 out of the system.

The introduction tube 210, the vial cap 100, and the collection vial 300 are made of plastics resistant to the modifier solvent to be used. For example, they can be produced at low cost by using polypropylene (PP), poly(ether ether ketone) (PEEK), or a fluororesin, such as a copolymer of tetrafluoroethylene and hexafluoropropylene (FEP), a copolymer of tetrafluoroethylene and perfluoroalkoxy ethylene (PFA), and a copolymer of tetrafluoroethylene and ethylene (ETFE), in accordance with the solubility of the modifier and molding any of the above materials in a mold.

The vial cap 100 and the collection vial 300 described above can be reused by cleaning them after they are used, but are single-used when sample collected before are hardly cleaned.

<Sample Collection Method>

The supercritical fluid system 2 including the sample collection apparatus with the sample collection containers according to the present invention is configured as described above, and a sample collection method using the sample collection containers will next be described with reference to FIGS. 2 to 7. As described above, among the components of the supercritical fluid system 2 shown in FIG. 2, the flow path switching valve 23 and the components upstream thereof are the same as those in the supercritical fluid system 1 of related art shown in FIG. 1. Therefore, no description of the flow path switching valve 23 and the components upstream thereof will be made. A large number of collection vials 300, each of which is provided with the vial cap 100, are held in the vial racks 45 in the sample collection apparatus 40 shown in FIG. 3.

Referring to FIG. 2, when the detector 20 does not detect any sample in the mixed fluid of the liquid-phase $CO_2$ and the modifiers delivered from the column 19, the mixed fluid passes through the automatic back pressure regulator 21, where the pressure of the mixed fluid is reduced to a pressure close to the atmospheric pressure. Therefore, the gas-phase $CO_2$ that undergoes adiabatic expansion aerosolizes the liquid component, which travels through the pre-heater 22 and is discharged out of the system through the flow path switching valve 23, as in the related art. When the detector 20 detects a first sample, and the flow path switching valve 23 is switched after a predetermined interval of time, the mixed fluid of the liquid-phase $CO_2$ and the modifier containing the detected first sample passes through the automatic back pressure regulator 21, where the pressure of the mixed fluid is reduced to a pressure close to the atmospheric pressure and the mixed fluid becomes an aerosol-containing gas similarly as described above, which is then heated by the pre-heater 22 and transferred through the flow path switching valve 23 toward the stainless steel tube 63 of the probe 60 connected to the resin tube 39.

The XYZ movement mechanism 41 moves the probe 60 in the X and Y directions to the position immediately above the collection vial 300 held in the holding hole 47 labeled with numeral 1 in one of the vial racks 45 shown in FIG. 4A. The stainless steel tube 63 is then lowered in the Z direction, and the probe distal end portion 61 comes into intimate contact with the inner wall 104 around the introduction hole 103 provided in the vial cap 100. The injection hole 62 in the probe distal end portion 61 is now connected to the introduction hole 103 in the vial cap 100.

The aerosol-containing gas is therefore transferred downward through the stainless steel tube 63 of the probe 60 via the resin tube 39. The gas is then transferred through the vial cap 100, which is in intimate contact with the probe distal end portion 61 located at the lower end of the stainless steel tube 63, into the introduction tube 210 attached to the bottom of the vial cap 100 and housed in the collection vial 300, as shown in FIG. 7. The gas is then sprayed in the circumferential but slightly downward direction along the inner circumferential surface 308 of the collection vial 300 through the distal end opening 211 of the introduction tube 210.

The gas containing the sprayed aerosol gradually falls while swirling along the inner circumferential surface 308 of the collection vial 300. In this process, the cylindrical collection vial 300 serves as a cyclone separator. That is, the liquid component in the form of aerosol dispersed in the gas-phase $CO_2$ collides with the inner circumferential surface 308 and is trapped thereon, and the gas-phase $CO_2$ is separated, rises in the collection vial 300, and exits through the discharge holes 109 in the vial cap 100 into the outer air. The liquid component trapped on the inner circumferential surface 308 grows into droplets, the diameter of which increases due to the successive collision of the liquid component, and the droplets flow downward and accumulate at the bottom of the collection vial 300. In this way, the liquid component containing the separated sample is collected at high collection efficiency.

When the detector 20 detects that the first separated sample is completely eluted from the column 19, the flow path switching valve 23 is switched to the position so that the flow path is to be the outside of the system, and the XYZ movement mechanism 41 lifts the stainless steel tube 63 from the collection vial 300 in the Z direction. The stainless steel tube 63 is then moved, for example, in the Y direction and stopped in the next position immediately above the adjacent collection vial 300. The stainless steel tube 63 is then lowered and the probe distal end portion 61 thereby comes into air-tight contact with the vial cap 100 on the adjacent collection vial 300.

Thereafter, when the detector 20 detects the next eluted sample, the flow path switching valve 23 is again switched to the position so that the flow path is connected to the probe 60, and the aerosol-containing gas formed in the components downstream of the automatic back pressure regulator 21 is delivered through the resin tube 39 into the stainless steel tube 63 of the probe 60 and dispensed into the adjacent collection vial 300. The same operation is repeated multiple times in correspondence with the number of contained samples by using a new collection vial 300 for each operation.

While the above description has been made by assuming that supercritical chromatography is used, the sample collection container of the present invention described above can be used in supercritical extraction. A supercritical fluid extraction apparatus can be provided by removing the injector 16 and replacing the column 19 with an extraction vessel (a vessel that encloses an extracted substance) in the supercritical fluid chromatographic apparatus 2 shown in FIG. 2. Further, the sample collection container of the present invention may be used in a case where the sample collection efficiency is insufficient in high-performance liquid chromatography.

INVENTION EXAMPLE

Figure 3:
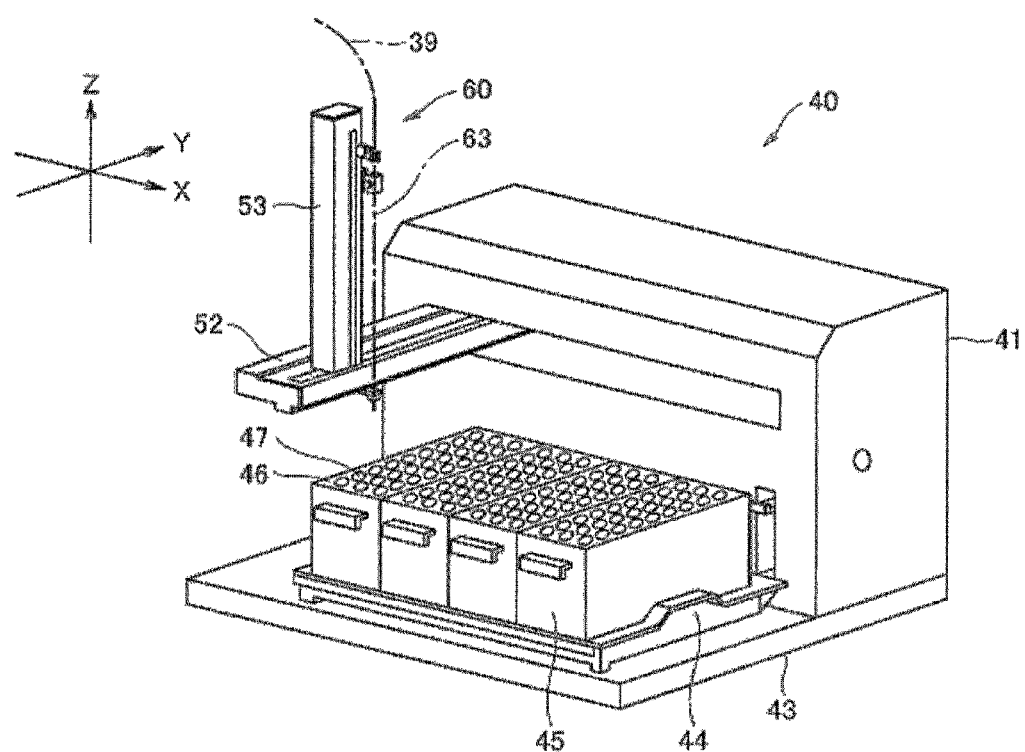
FIG. 3 is an overall perspective view showing a sample collection apparatus.
Figure 4:
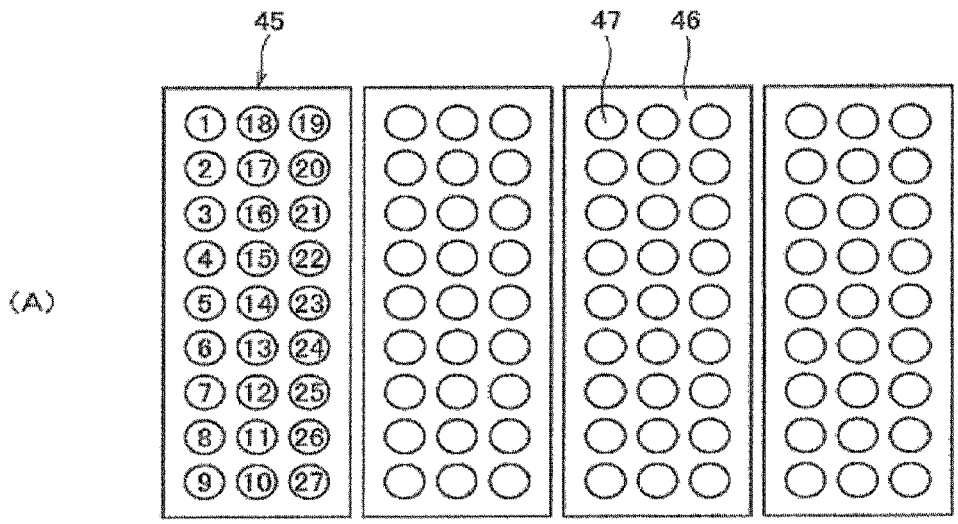
FIGS. 4A and 4B show vial racks, FIG. 4A being a plan view showing an example of how holding holes are arranged in four vial racks and FIG. 4B being a perspective view of any one of the vial racks.
Figure 4:
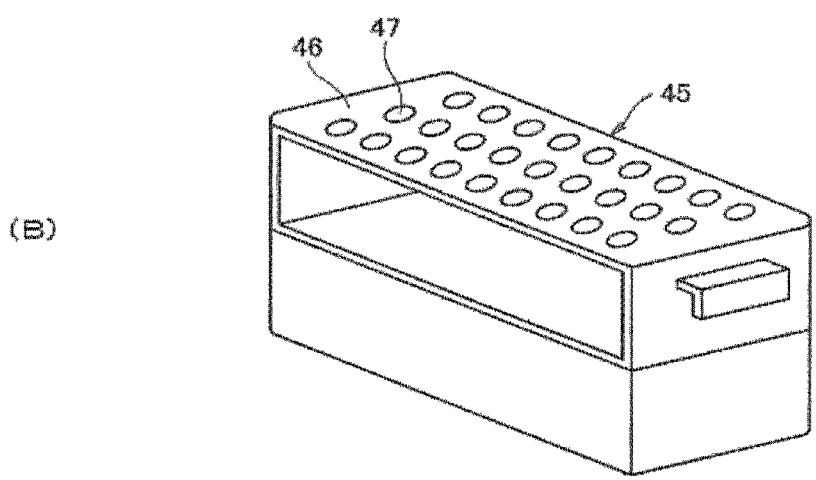
Figure 5:
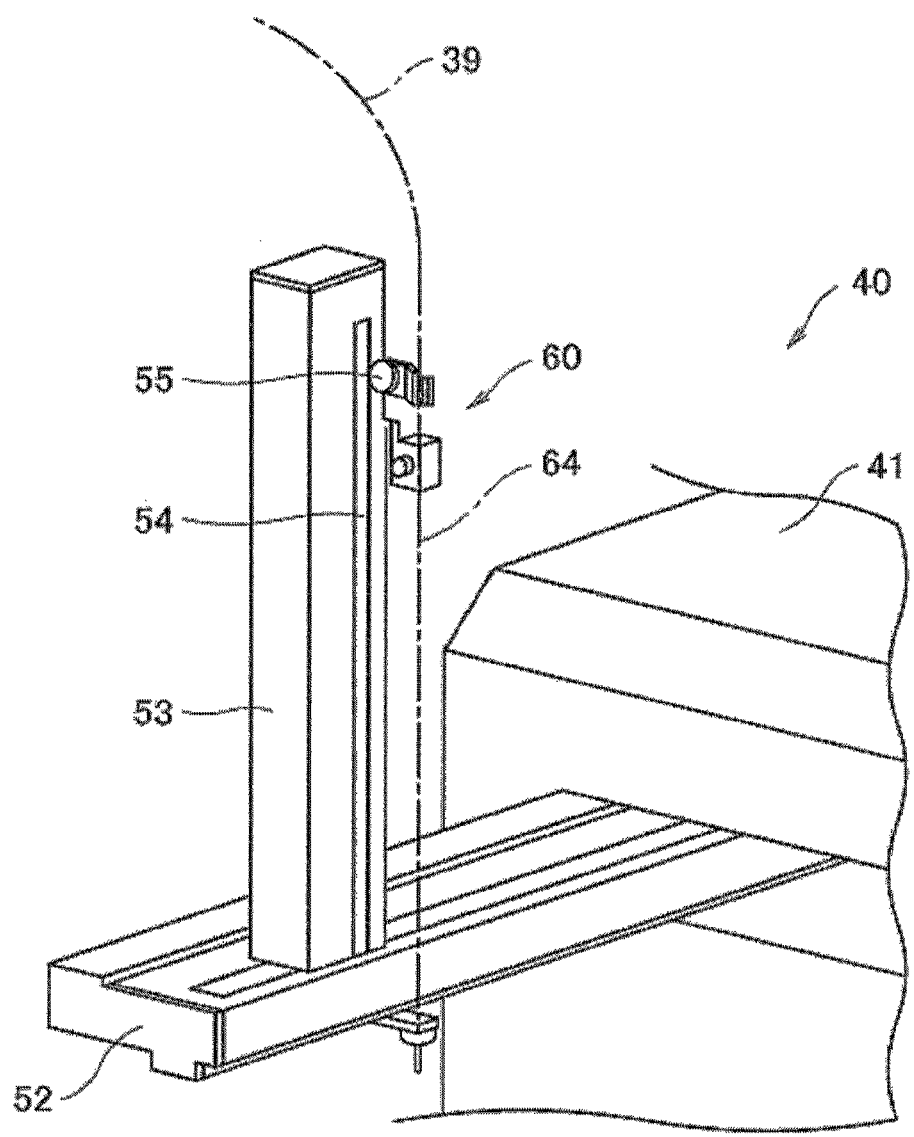
FIG. 5 is an enlarged perspective view showing an XYZ movement mechanism including a probe.
Figure 6:
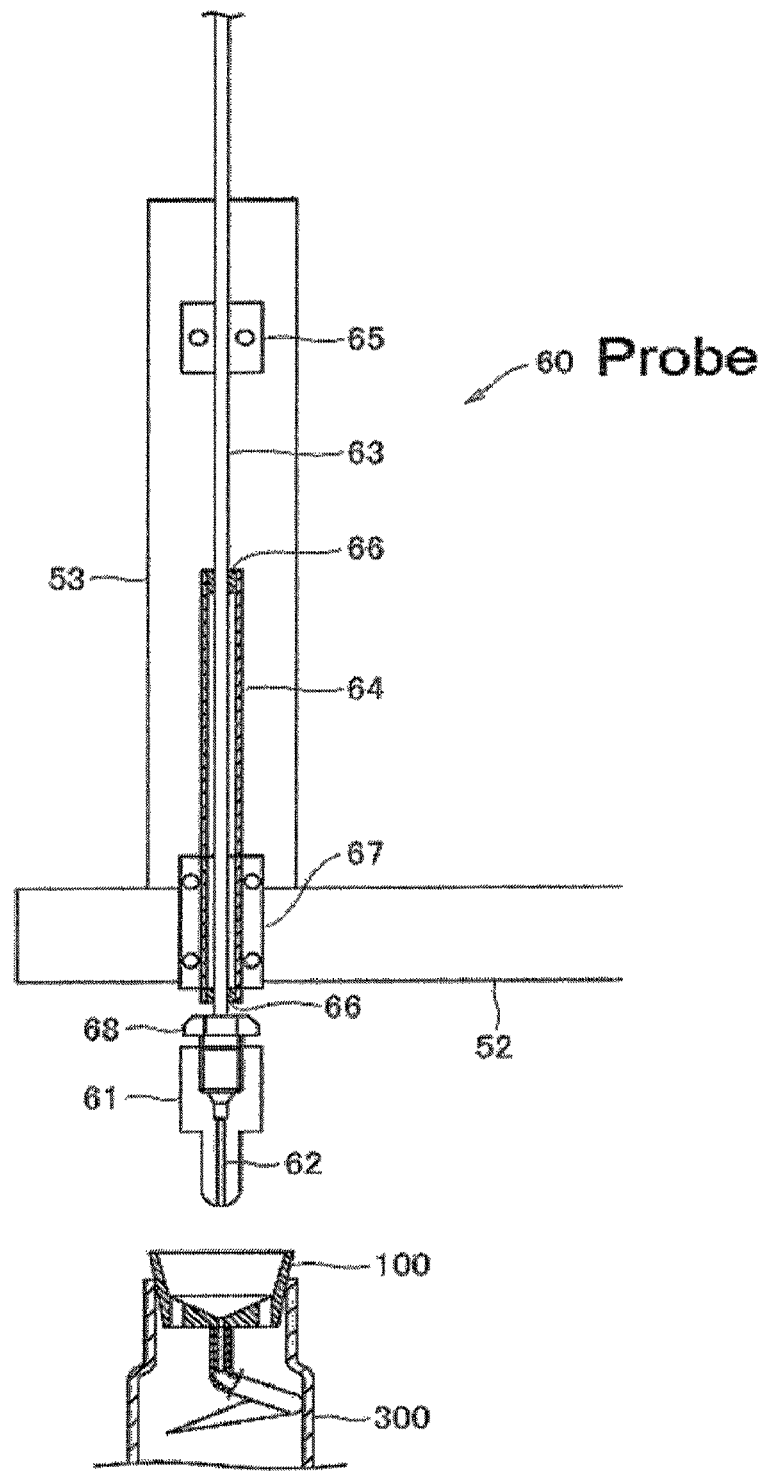
FIG. 6 is a partial cutaway view showing the probe.

The XYZ movement mechanism 41, which is the "Liquid Handler" that moves the probe 60 shown in FIG. 3, was used to attempt to collect a sample (warfarin) in the supercritical chromatographic apparatus 2 shown in FIG. 2. That is, a test of whether the sample is collected in any of the collection vials 300 was carried out by lowering the probe distal end portion 61 shown in FIG. 7, which is connected to the stainless steel tube 63, and bringing the probe distal end portion 61 into intimate contact with the inner wall 104 of the vial cap 100. The following mixed fluid was used as the mobile phase of supercritical fluid chromatography, and the change in sample collection efficiency versus the flow rate of the supercritical fluid was determined under the following conditions:

| [Mobile Phase] | |
|---|---|
| Mobile Phase | $CO_2$/ethyl alcohol (modifier) |
| Flow Rate | 5 g/min/0.5 mL/min |
| | 10 g/min/1.0 mL/min |
| | 30 g/min/3.0 mL/min |
| | 50 g/min/5.0 mL/min |
| [Column] | |
| Temperature | 40° C. |
| [Sample and amount of injection] | |
| Sample | Solution of 100.0 mg of warfarin in 50 mL of ethyl alcohol |
| Injection Volume | 10 μL |
| [Pressure] | |
| Pressure | 20 MPa |

| [UV detector] | |
|---|---|
| Flow cell | High pressure resistant cell (optical path length of 5 mm) |
| Wavelength | UV 280 nm |

Table 1 shows the sample collection efficiency versus the flow rate of the supercritical fluid under the conditions described above. Since the test was carried out to check the collection efficiency by using pure warfarin, the number of fractionated components is one, and only one collection vial 300 was used.

TABLE 1

Sample collection efficiency versus flow rate of supercritical fluid in Invention Example

| Flow rate of $CO_2$ g/min | Flow rate of ethyl alcohol mL/min | Sample collection efficiency % |
|---|---|---|
| 5 | 0.5 | 98 or more |
| 10 | 1.0 | 98 or more |
| 30 | 3.0 | 98 or more |
| 50 | 5.0 | 95 or more |

COMPARATIVE EXAMPLE

For comparison purposes, the "Liquid Handler" was used to carry out a test of whether a sample is collected by forcing a stainless steel tube attached to the tip of the probe 60 to penetrate through a septum interposed between a commercially available collection vial and a screw cap with an opening. The septum was precut in advance to discharge gas-phase $CO_2$. Table 2 shows the sample collection efficiency versus the flow rate of the supercritical fluid in this case.

TABLE 2

Sample collection efficiency versus flow rate of supercritical fluid in Comparative Example

| Flow rate of $CO_2$ g/min | Flow rate of ethyl alcohol mL/min | Sample collection efficiency % |
|---|---|---|
| 5 | 0.5 | 88 |
| 8 | 0.8 | 75 |
| 20 | 2.0 | 56 |

Comparison between Table 1 and Table 2 shows that when the flow rate of the supercritical fluid is as low as 5 g of $CO_2$ per minute and 0.5 mL of ethyl alcohol per minute, the collection efficiency is 98% or greater in Invention Example, whereas the sample collection efficiency is only 88% in Comparative Example. Further, the collection efficiency decreases to 56% in Comparative Example when the flow rate of the supercritical fluid is increased to 20 g of $CO_2$ per minute and 2.0 mL of ethyl alcohol per minute. In contrast, the collection efficiency is 98% or greater in Invention Example when the flow rate of the supercritical fluid is increased to 30 g of $CO_2$ per minute and 3.0 mL of ethyl alcohol per minute, clearly showing a significant improvement in sample collection efficiency in the sample collection method using the apparatus of the present invention.

Comparative Example greatly differs from Invention Example in that an aerosol-containing gas is sprayed downward into the commercially available, typical collection vial through the tip of the stainless steel tube. Therefore, the aerosol having reached the bottom of the collection vial is reversed, and the gas-phase $CO_2$ rises toward the discharge cutout and exits therethrough. In this case, the liquid component in which the sample is dissolved accumulates at the bottom of the collection vial, whereas part of the liquid component is discharged along with the $CO_2$ through the discharge cutout as the flow of the aerosol is reversed. The sample collection efficiency therefore decreases. In contrast, in Invention Example, since the collection vial 300 serves as a cyclone separator, the gas-phase $CO_2$ is removed through the discharge holes 109 in the vial cap 100 into the outer air, whereas the liquid component in which the sample is dissolved collides with the inner circumferential surface 308 of the collection vial 300, is trapped thereon, and grows into droplets with increased diameters, which move to the bottom, and accumulate there. The liquid component in which the sample is dissolved is therefore collected at high collection efficiency.

Example Embodiment 1

The introduction tube 210 shown FIG. 7 has a straight portion extending downward from the center of the bottom surface of the vial cap 100 and a subsequent portion extending sideward along the inner circumferential surface 308 of the collection vial 300 and having a length shorter than or equal to the circumferential length of the inner circumferential surface 308. The introduction tube may alternatively be a spiral introduction tube 220 that swirls along the inner circumferential surface 308 of the collection vial 300 once or twice and is slightly inclined downward (preferably inclined downward by 5 to 20 degrees from the horizontal tangential direction), as shown in FIG. 9. In this case, since the aerosol-containing gas flowing in the spiral introduction tube 220 exerts a force that enlarges the circumference thereof, the tip of the spiral introduction tube 220 is stably in contact with the inner circumferential surface 308 of the collection vial 300.

Since the gas-phase $CO_2$ rises in a central portion of the collection vial 300, the liquid component having accumulated at the bottom of the collection vial 300 accompanies the gas-phase $CO_2$ and rises along the inner circumferential surface 308. The spiral introduction tube 220 in intimate contact with the inner circumferential surface 308 of the collection vial 300 serves to block the rising liquid modifier and cause the liquid component to return downward. In this way, the liquid modifier will not scatter through the discharge holes 109 in the vial cap 100 along with the gas-phase $CO_2$, whereby the sample collection efficiency will not decrease.

Example Embodiment 2

In the Example Embodiment 1 of the vial cap, the introduction tube 220 swirls once or twice along the inner circumferential surface 308 of the collection vial 300. Alternatively, an O-ring 311 having an outer diameter that is the same as the diameter of the inner circumferential surface 308 may be attached to an upper end portion of the inner circumferential surface 308 of a collection vial 310, as shown in FIG. 10. The O-ring enables to suppress the liquid component rising along the inner circumferential surface 308 of the collection vial 310.

Example Embodiment 3

While the tip of the probe distal end portion 61 has a hemispherical shape in FIGS. 7 and 8, a probe distal end portion 71 with a conical tip may alternatively be attached to the lower end of the stainless steel tube 63, as shown in FIG. 11, and the probe distal end portion 71, when lowered, may come into intimate contact with a conical inner wall 114 of a vial cap 110. An injection hole 72 is formed along the axis of the probe distal end portion 71.

Example Embodiment 4

FIG. 12 shows a collection vial 320 and a vial cap 120. That is, the collection vial 320 has a cylindrical shape, and a flange 126 provided at the periphery of a body 121 of the vial cap 120 is placed on the edge of an upper end opening 321 of the collection vial 320. An upper end portion of the introduction tube 210 is fitted in and fixed to the outer circumferential surface of an attachment tube 125 protruding from a central portion of a bottom portion 122, as in the case shown in FIGS. 7 and 8. Discharge holes 129 are formed as through holes extending from the bottom surface of the vial cap 120 to the top surface of the vial cap 120. As a result of combining the cylindrical collection vial 320 with the vial cap 120 having the flange 126 as described above, the resultant collection unit is more readily assembled and disassembled, and the workability is improved particularly when a large number of collection vials are set.

Example Embodiment 5

Alternatively, a rotating introduction tube that rotates around the attachment tube provided on the bottom surface of the vial cap may be attached, as shown in FIGS. 13A and 13B. FIG. 13A shows the vial cap 120 combined with the collection vial 320 shown in FIG. 12 and a grooved attachment tube 135 protruding from the central portion of the bottom portion 122 of the vial cap 120. A circumferential guide groove 136 is provided by cutting the outer circumferential surface of the grooved attachment tube 135. A perforated circular plate 231 has a hole 232 and is attached to the upper end of the rotating introduction tube 230. And, the plate 231 is fitted in the guide groove 136 via the hole 232.

FIG. 13B is a cross-sectional view taken along the line [B]-[B] shown in FIG. 13A. As shown in FIG. 13B, when an aerosol-containing gas is sprayed out of the tip of the rotating introduction tube 230 in the p direction, a reaction force rotates the rotating introduction tube 230 around the attachment tube 135 in the q direction. As a result, the aerosol can be uniformly sprayed in all directions toward an inner circumferential surface 328 of the collection vial 320, and the speed at which the aerosol is sprayed toward the inner circumferential surface 328 can be reduced.

Example Embodiment 6

FIGS. 14A and 14B show a collection vial 330 having a short, wide-mouth neck 332 and a vial cap 140. That is, FIG. 14A is a plan view showing the vial cap 140 placed on the collection vial 330, and FIG. 14B is a cross-sectional view taken along the line [B]-[B] shown in FIG. 14A. As shown in FIG. 14B, the vial cap 140 is placed on the end of the opening of the short, wide-mouth neck 332. The vial cap 140 includes a funnel-shaped body 141 with discharge holes 149 at the periphery, a flange 146 around the outer circumference of the body 141, a cylindrical skirt 147 extending downward from the bottom surface of the flange 146, and an introduction tube 240. The components described above are integrally formed into the vial cap 140.

Since the body 141 having a conical inner wall 144 and the introduction tube 240 are shaped substantially similarly to those in the other examples, no redundant description thereof will be made. As shown in FIG. 14A, the discharge holes 149 are formed at three locations at equal angular spacings in a boundary portion between the body 141 and the outer circumferential flange 146. The skirt 147 is not in contact with the inner circumferential surface of the wide-mouth neck 332 of the collection vial 330.

As described above, since the skirt 147 serves as a barrier that prevents the liquid modifier rising an inner circumferential surface 338 of the collection vial 330 from entering the discharge holes 149, the liquid component does not exit through the discharge holes 149 to the outside and no collection loss occurs. Further, since the discharge holes 149 are provided at the periphery of the funnel-shaped body 141 and the upper end opening of each of the discharge holes 149 is lower than the upper end of the funnel-shaped body 141, any liquid modifier attached to the periphery of the upper end opening of each of the discharge holes 149 does not flow into the funnel-shaped body 141 and thus does not contaminate the sample dispensed into the body 141.

Example Embodiment 7

Figure 9:
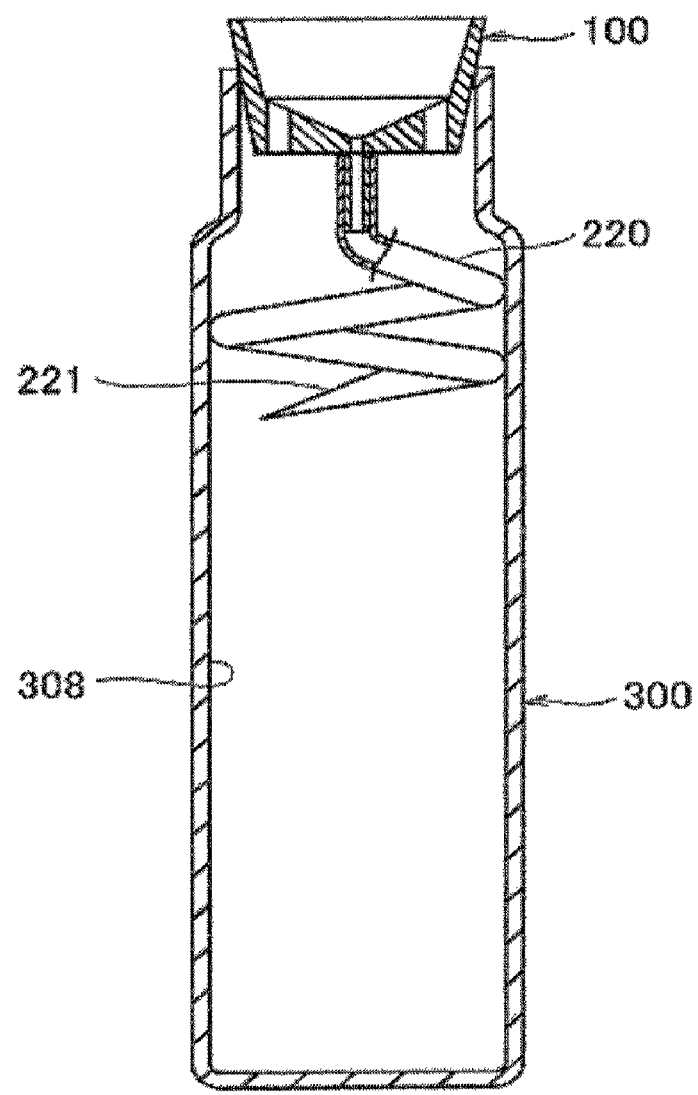
FIG. 9 is a cross-sectional view showing a spiral introduction tube.
Figure 10:
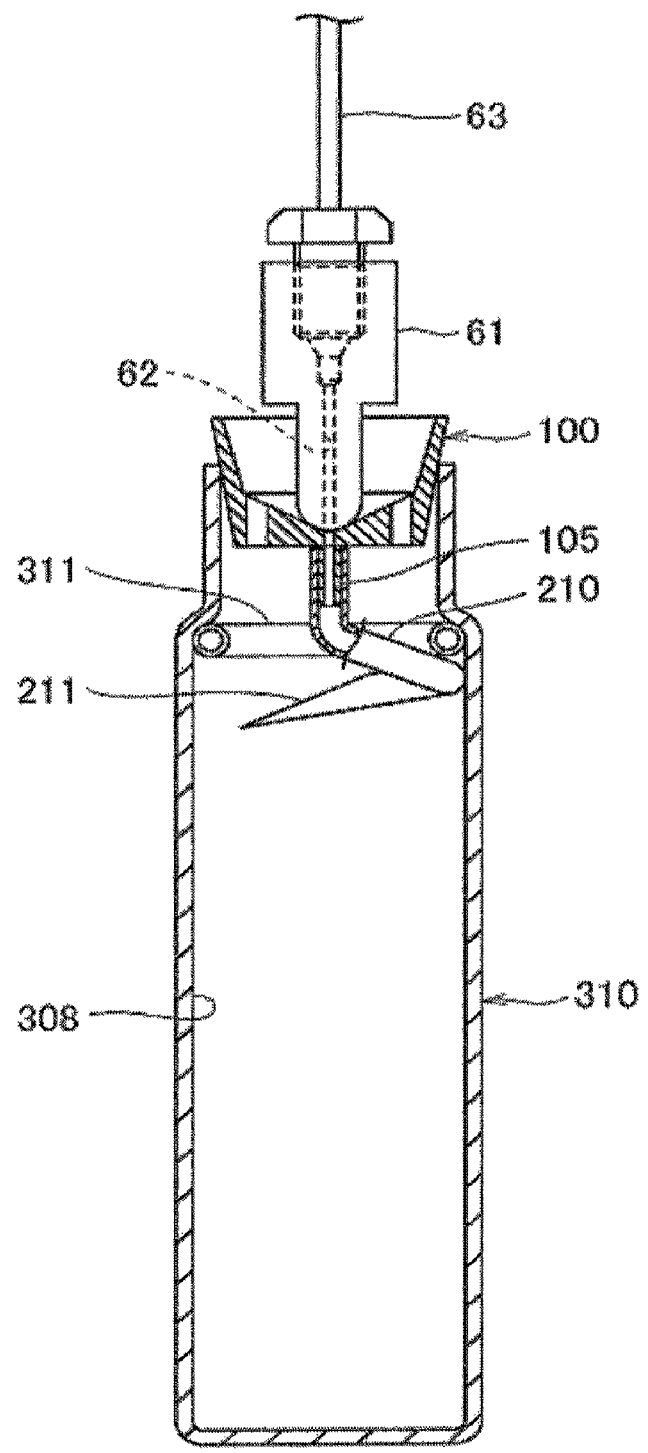
FIG. 10 is a cross-sectional view showing a collection vial with an O-ring provided on the inner circumferential surface.
Figure 15:
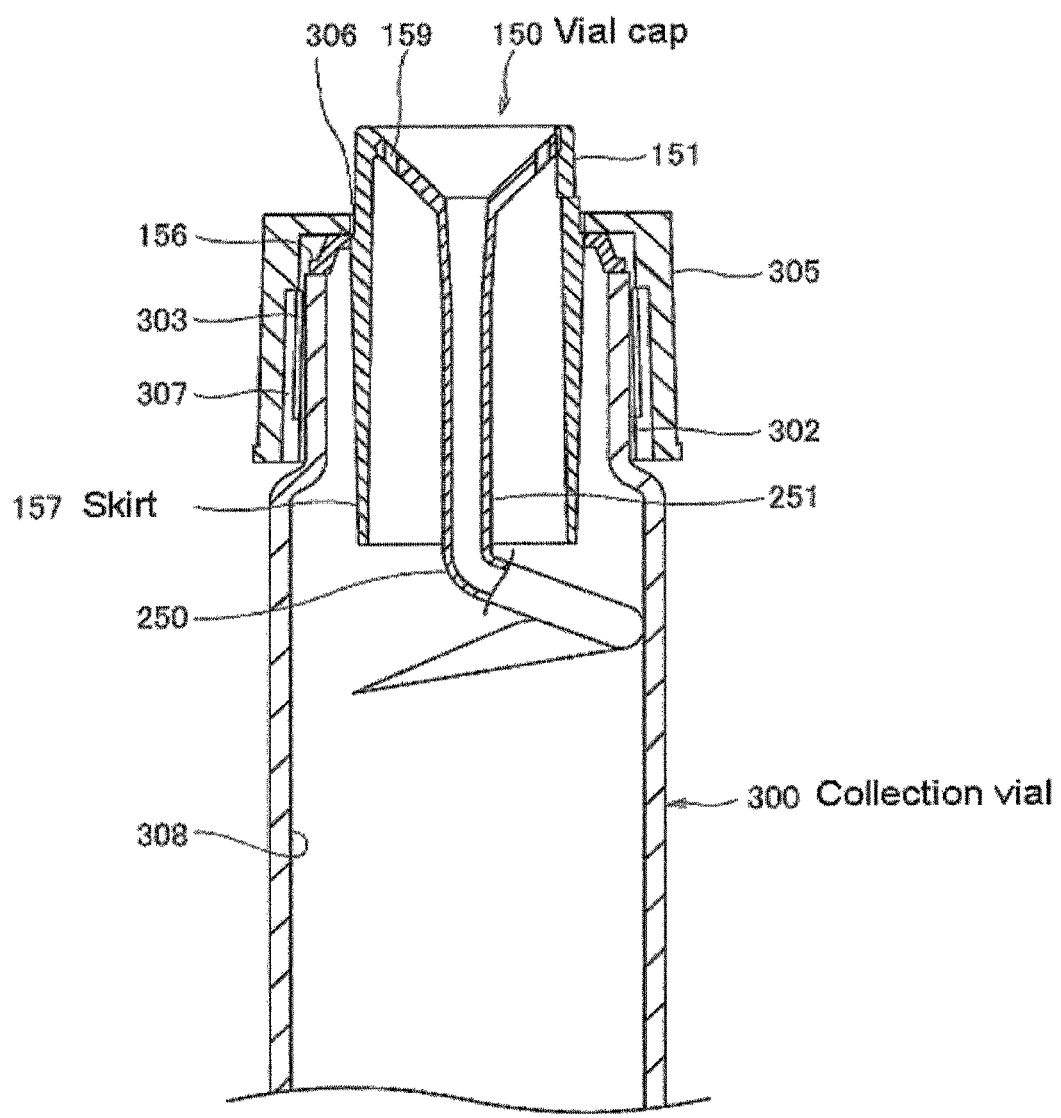
FIG. 15 is a cross-sectional view showing a vial cap having another exemplary different shape.

FIG. 15 is a cross-sectional view showing the collection vial 300, which is the same as those shown in FIGS. 7, 9, and 10, that is, the collection vial 300 formed of the body 301 and the wide-mouth neck 302, and a vial cap 150 placed on and fixed to the edge of the opening of the wide-mouth neck 302. The vial cap 150 includes a funnel-shaped body 151 with discharge holes 159 formed on the upper end side, an introduction tube 250 with a long straight portion 251 extending downward from and formed integrally with a central bottom portion of the body 151, a cylindrical skirt 157 extending from the bottom surface of the periphery of the body 151 and surrounding the straight portion 251 of the introduction tube 250, and a flange 156 formed at the periphery of the upper end of the skirt 157. The components described above are integrally formed into the vial cap 150. The flange 156 of the vial cap 150 is placed on the edge of the opening of the wide-mouth neck 302 of the collection vial 300.

As shown in FIG. 15, the vial cap 150 is fixed to the collection vial 300 with a perforated screw cap 305. That is, the top portion of the perforated screw cap 305 has a hole 306 into which the body 151 of the vial cap 150 is inserted, and the inner circumferential edge of the hole 306 presses and secures the upper surface of the flange 156 of the vial cap 150. A female thread 307 provided on the inner wall of the perforated screw cap 305 engages a male thread 303 formed on the outer circumferential surface of the wide-mouth neck 302. The vial cap 150 is thus fixed to the collection vial 300.

Since the skirt 157 of the thus configured vial cap 150 again serves as a barrier that prevents the liquid component rising along an inner circumferential surface 308 of the collection vial 300 from entering the discharge holes 159, the liquid modifier does not exit through the discharge holes 159 to the outside and no collection loss occurs.

Example Embodiment 8

Figure 16:
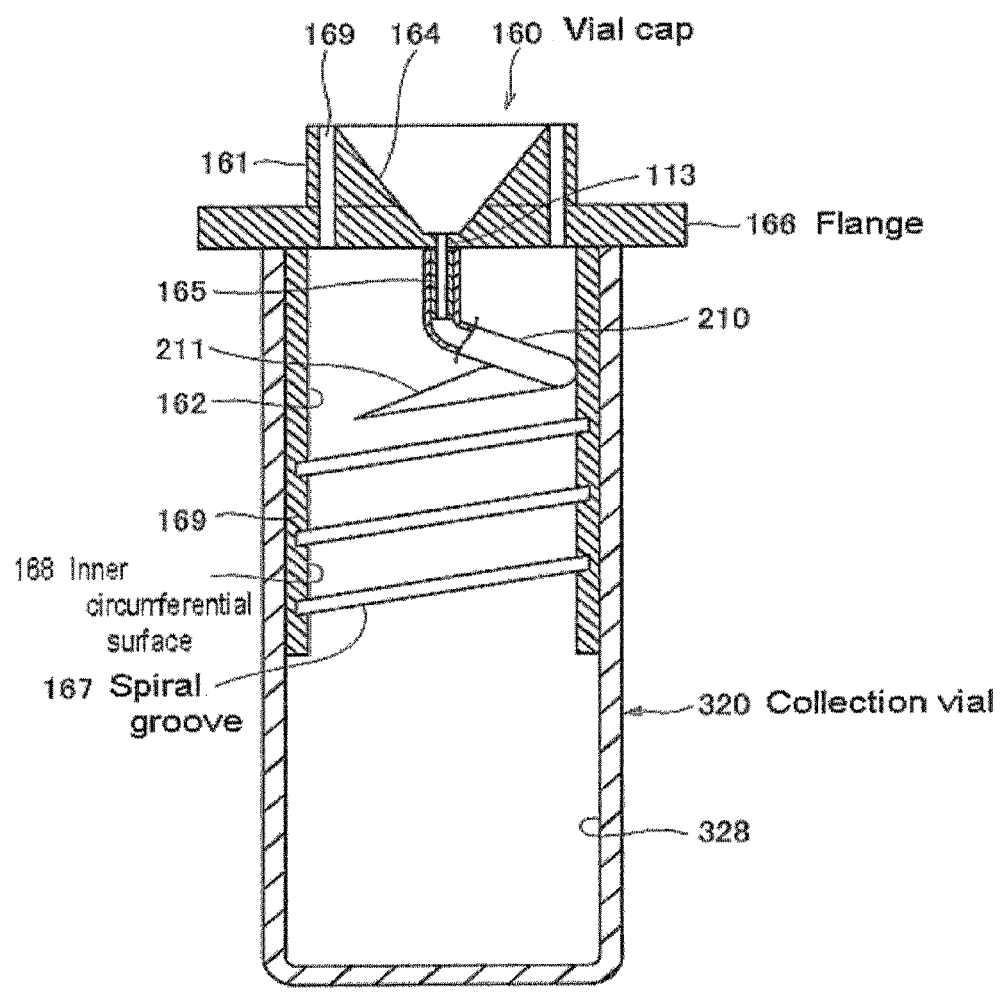
FIG. 16 is a cross-sectional view showing a vial cap having another exemplary different shape.

FIG. 16 is a cross-sectional view showing the cylindrical collection vial 320 and a vial cap 160 placed on the edge of the opening of the collection vial 320. As shown in FIG. 16, the vial cap 160 includes a body 161 having a conical inner wall 164 and discharge holes 169, a flange 166 provided at the periphery of the body 161, an attachment tube 165 protruding downward from a central portion of a bottom portion of the body 161, the introduction tube 210, an upper end portion of which fits on the outer circumferential surface of the attachment tube 165, and a cylindrical member 162 extending downward from the lower surface of the flange 166 and inserted into the collection vial 320 in such a way that the cylindrical member 162 comes into contact with the inner circumferential surface 328 of the collection vial 320. A spiral groove 167 slightly inclined downward (preferably inclined downward by 5 to 10 degrees from the horizontal direction) is formed in an inner circumferential surface 168 of the cylindrical member 162.

An aerosol-containing gas dispensed into the body 161 of the vial cap 160 exits out of the distal end opening 211 of the introduction tube 210 and spirally swirls downward while being guided along the spiral groove 167 in the cylindrical member 162. In this process, the liquid component collides with the inner circumferential surface 168 of the cylindrical member 162 and is trapped thereon, which grows into droplets, the diameter of which increases due to the successive collision of the liquid component. The thus formed droplets fall, whereas the gas-phase $CO_2$ rises and exits through the discharge holes 169. The spiral groove 167 formed in the cylindrical member 162 helps the aerosol-containing gas to swirl, which facilitates trapping the liquid component and contributes to improvement in the sample collection efficiency.

Example Embodiment 9

Figure 11:
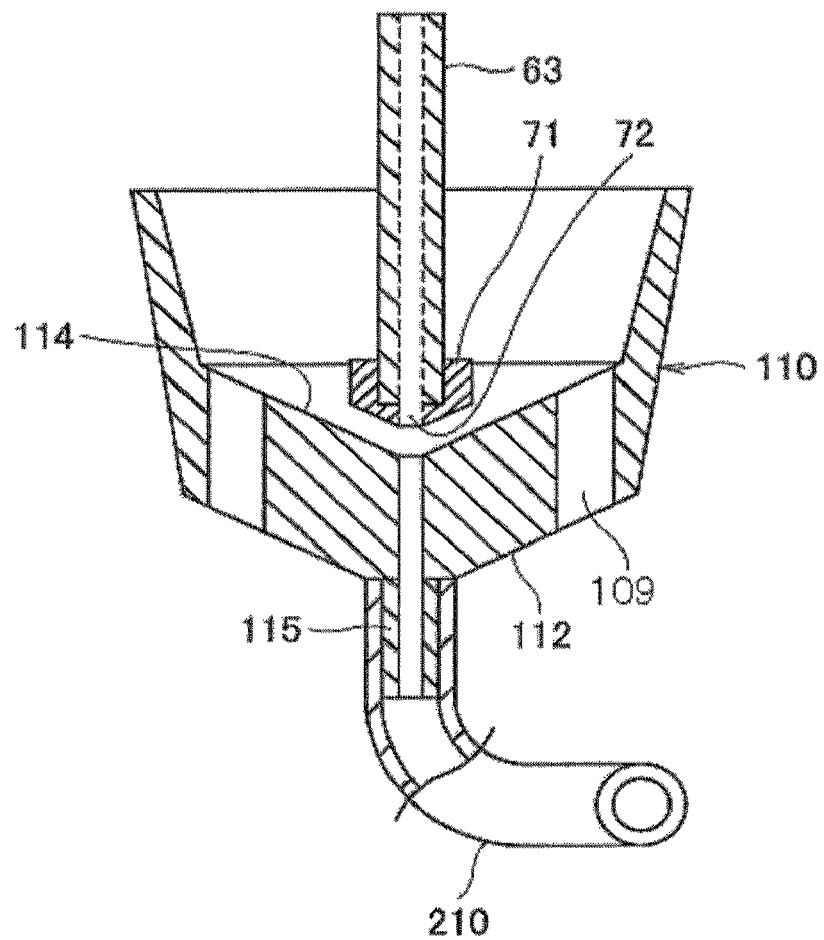
FIG. 11 is a cross-sectional view showing a probe having a truncated conical tip.
Figure 12:
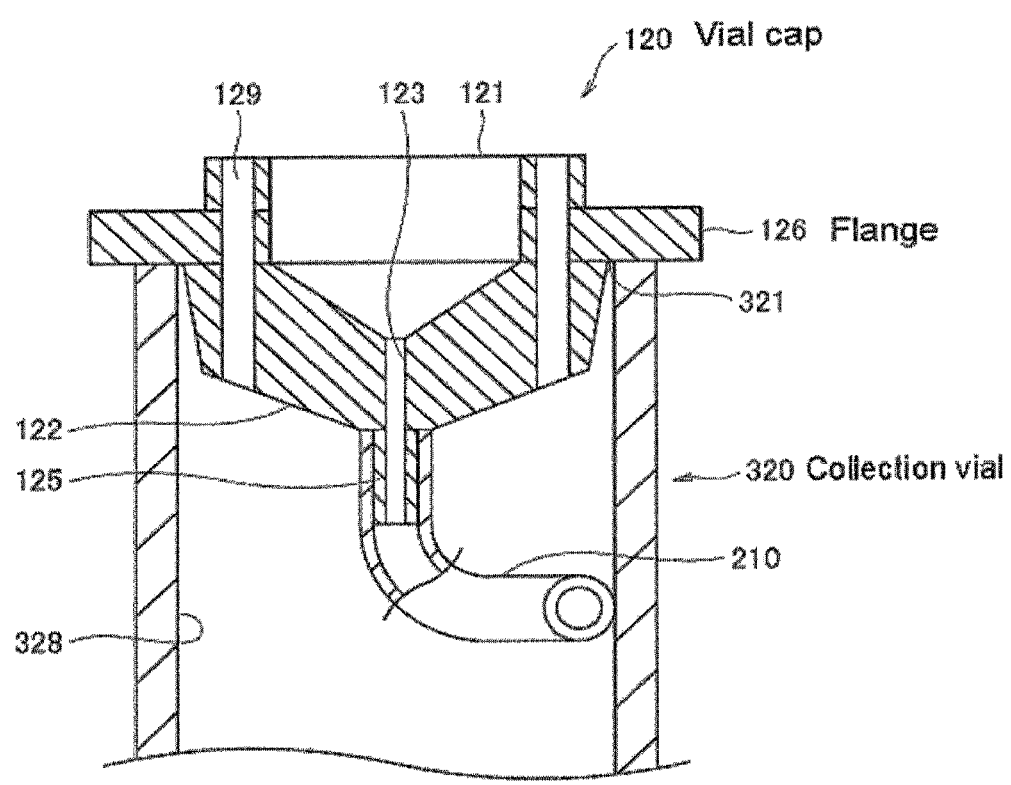
FIG. 12 is a cross-sectional view showing an example of a collection vial having an exemplary different shape combined with a vial cap having an exemplary different shape.
Figure 13:
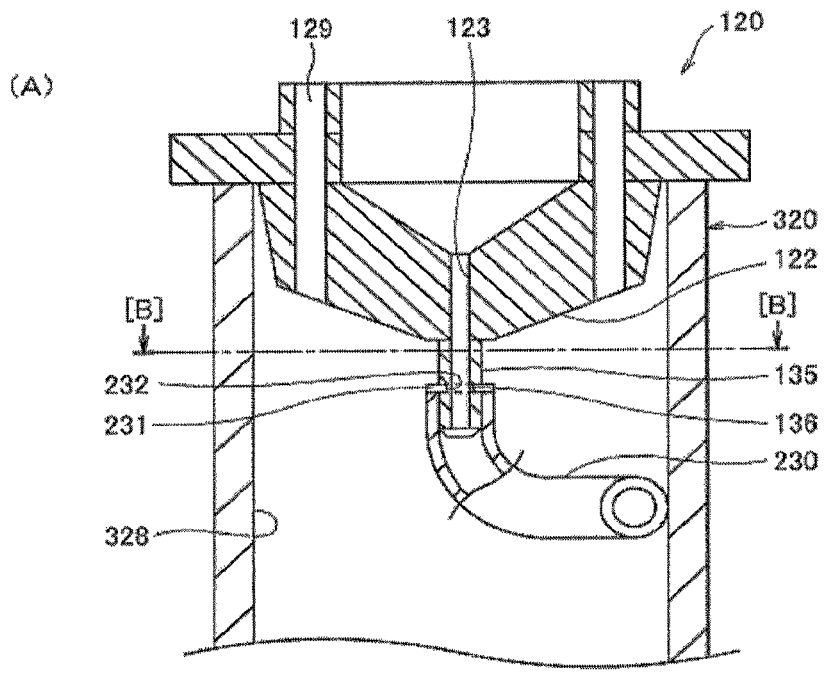
FIGS. 13A and 13B are cross-sectional views showing a rotating introduction tube.
Figure 13:
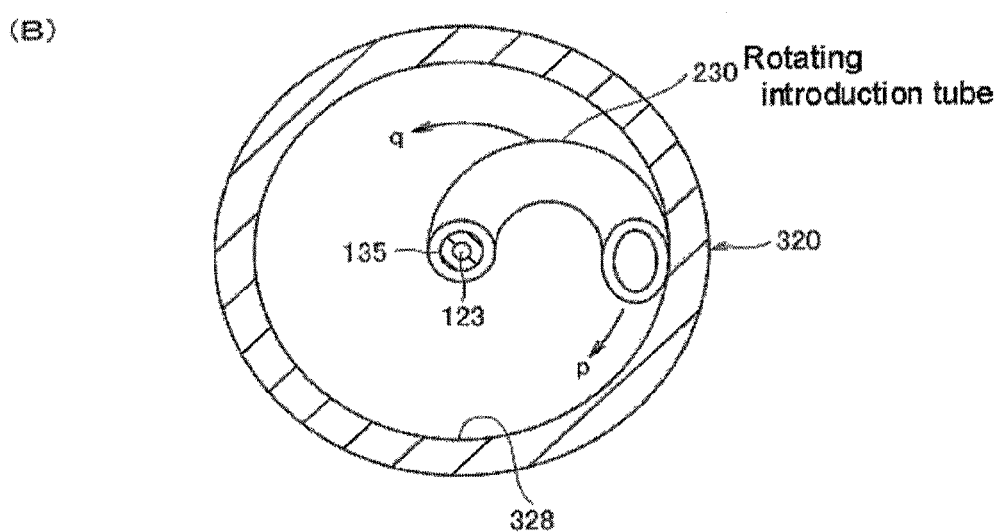
Figure 14:
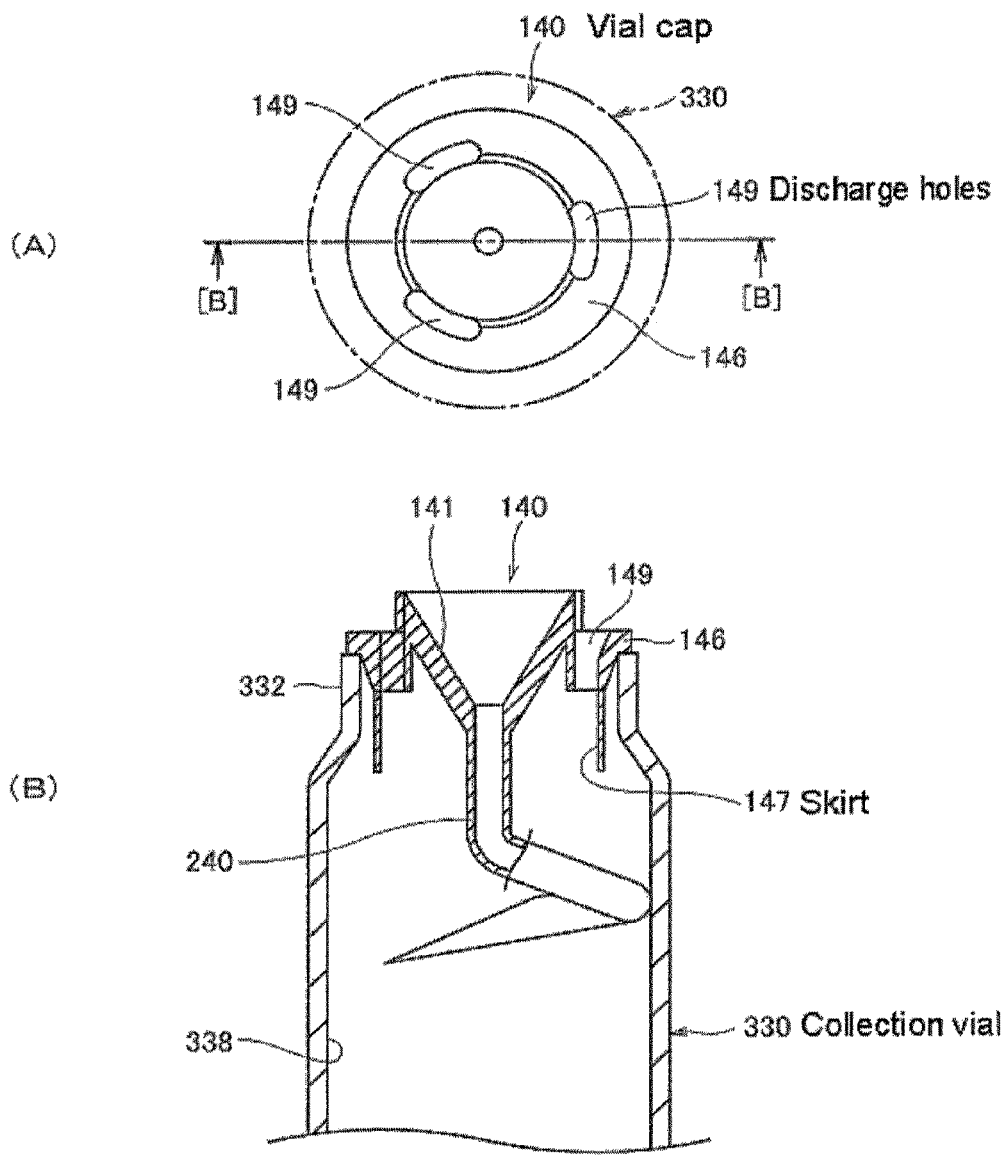
FIGS. 14A and 14B are cross-sectional views showing a vial cap having another exemplary different shape.
Figure 17:
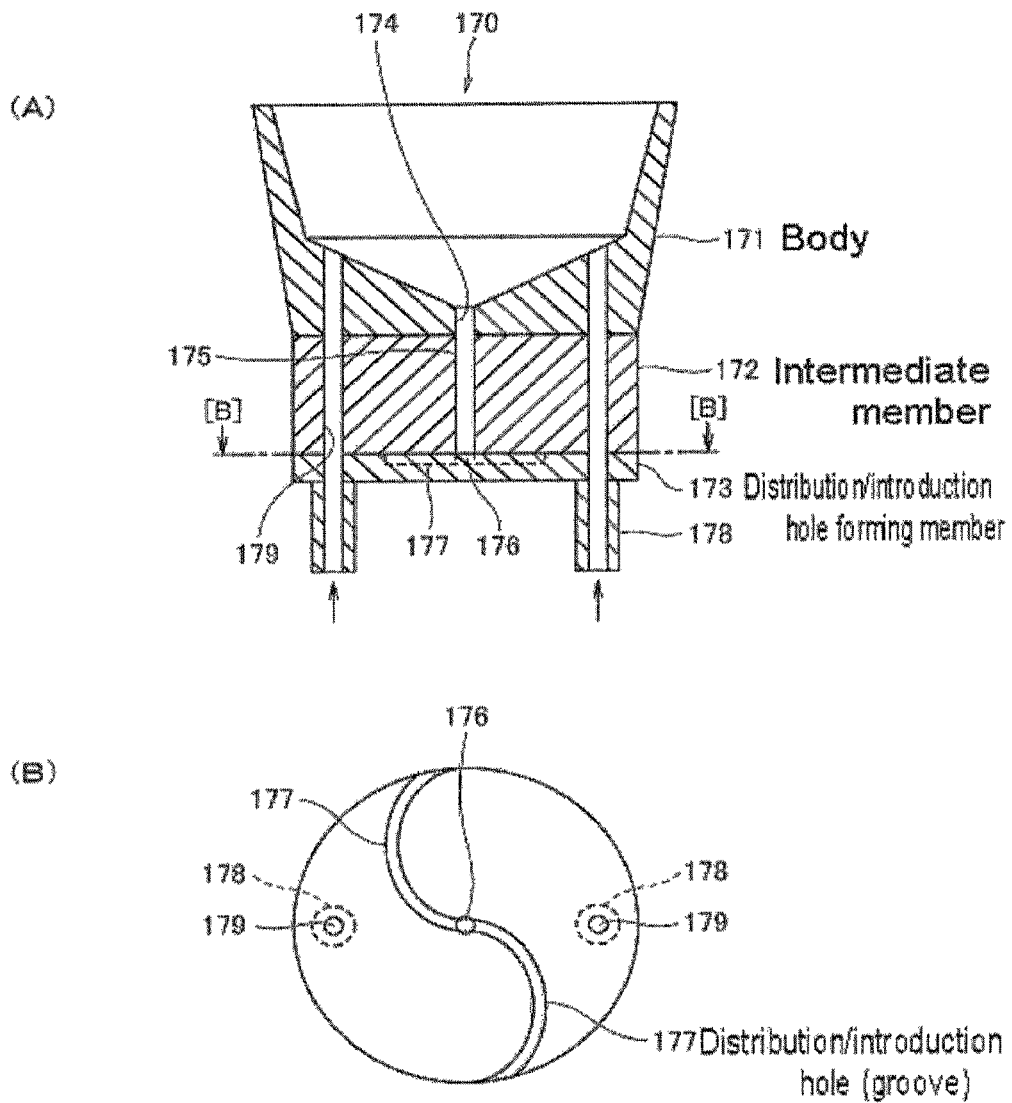
FIGS. 17A and 17B show a vial cap with two horizontal distribution holes provided therein, FIG. 17A being a longitudinal cross-sectional view showing a three-layer configuration of the vial cap and FIG. 17B being a cross-sectional view of the vial cap taken along the line [B]-[B] shown in FIG. 17A, that is, a plan view of a lower layer.

A vial cap 170 shown in FIGS. 17A and 17B differs from the vial caps shown in FIGS. 8 and 11 in that an aerosol-containing gas is not sprayed through an introduction tube, but sprayed through arcuate distribution holes 177 provided in the vial cap 170. FIG. 17A is a longitudinal cross-sectional view of the vial cap 170. As shown in FIG. 17A, the vial cap 170 includes a body 171, an intermediate member 172, and a distribution hole forming member 173. The components described above are integrally formed into the vial cap 170. FIG. 17B is a cross-sectional view of the vial cap 170 taken along the line [B]-[B] shown in FIG. 17A, that is, a plan view of the member 173. Among the above components, since the body 171 is similar to the body 101 of the vial cap 100 shown in FIG. 8, no redundant description thereof will be made. The intermediate member 172 is a cylindrical member with a introduction hole 175 drilled therein, the introduction hole 175 connecting with an introduction hole 174 in the body 171.

As shown in FIG. 17B, the member 173 has a central portion 176 and two arcuate symmetrical distribution holes 177 (showed as grooved in FIG. 17B) formed in the upper surface that is in intimate contact with the bottom surface of the intermediate member 172. The central portion 176 corresponds to the lower end of the introduction hole 175, and the two arcuate symmetrical distribution holes 177 extending from the central portion 176 to the outer circumferential surface of member 173 are formed symmetrically with respect to the central portion 176. Therefore, the intermediate member 172 overlaid on the member 173 forms the distribution holes 177.

The aerosol-containing gas injected into the introduction hole 174 in the body 171 travels through the introduction hole 175 in the intermediate member 172, is distributed through the central portion 176 into the two distribution holes 177 in the member 173, and is sprayed in the tangential direction out of the openings of the distribution holes 177 in the outer circumferential surface of the member 173 to the inner circumferential surface of the collection vial (not shown).

The distribution holes 177 thus formed in the vial cap 170 do not vibrate or deform, unlike an introduction tube, due to variation in the spray speed, for example, at the time when aerosol introduction starts, whereby the aerosol is sprayed in a stable manner. Further, since the aerosol-containing gas dispensed through the introduction hole 174 is distributed into the two distribution holes 177, the speed at which the aerosol is sprayed out of the opening of each of the distribution holes 177 is reduced to approximately half the speed when an introduction tube is used, whereby the amount of loss due to scattering is reduced.

As shown in FIGS. 17A and 17B, the vial cap 170 also has two discharge holes 179 provided through the member 173, the intermediate member 172, and the body 171 to remove the gas-phase $CO_2$ rising in the collection vial (not shown). Additionally, two discharge tubes 178 protrude downward from the bottom surface of the member 173, as shown in FIG. 17A. The discharge tubes 178 is connects with the discharge holes 179. Therefore, the gas-phase $CO_2$ rising from below travels through hollow holes in the discharge tubes 178 and then the discharge holes 179 and exits out of the system.

If the gas-phase $CO_2$ is discharged through the lower end of the discharge holes 179 in the structure that the discharge tubes 178 are not provided, the aerosol exited out of the distribution holes 177 tends to accompany the gas-phase $CO_2$ and be sucked into the discharge holes 179, because the level at which the openings of the distribution holes 177 are located is close to the level at which the lower ends of the discharge holes 179 are located. The discharge tubes 178 prevent the collection loss from occurring.

The aerosol-containing gas sprayed in the tangential direction out of the openings of the distribution holes 177 to the inner circumferential surface of the collection vial (not shown) swirls along the inner circumferential surface of the collection vial and falls downward. The liquid component collides with the inner circumferential surface of the collection vial and is trapped thereon, as in the other examples described above. While the two arcuate distribution holes 177 are provided in FIGS. 17A and 17B, three distribution holes 177 may be provided at equal angular spacings of approximately 120 degrees, or even four or more distribution holes 177 may be provided. Further, the intermediate member 172 and the member 173 may be integrally formed.

Example Embodiment 10

Figure 18:
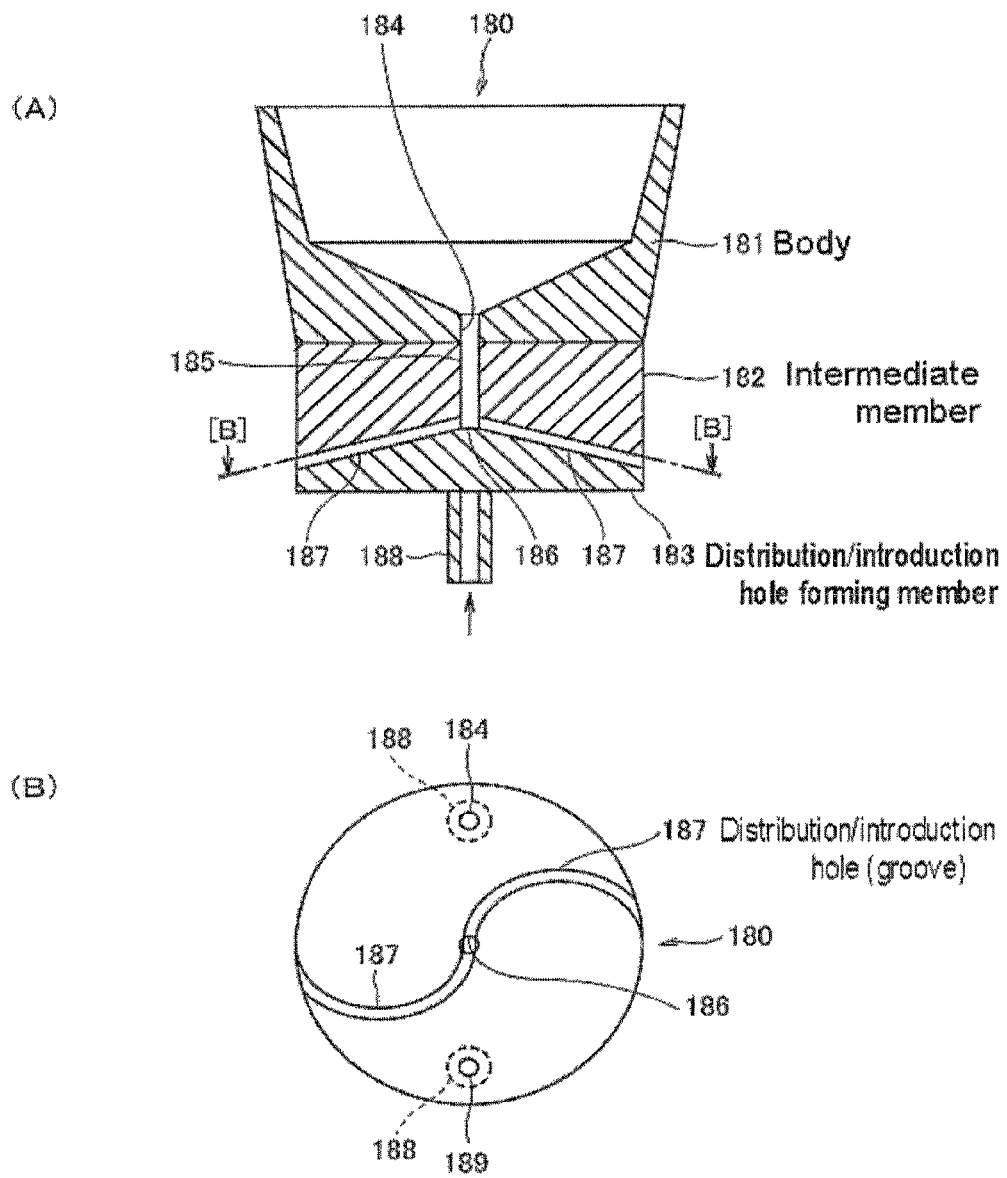
FIGS. 18A and 18B show a vial cap with two distribution holes provided along a conical plane, FIG. 18A being a longitudinal cross-sectional view showing a three-layer configuration of the vial cap and FIG. 18B being a cross-sectional view of the vial cap taken along the line [B]-[B] shown in FIG. 18A, that is, a plan view of a lower layer.

FIGS. 17A and 17B show the vial cap 170 with the two horizontal arcuate distribution holes 177. As an example embodiment therefrom, two distribution holes 187 may be provided along a conical plane, as shown in FIGS. 18A and 18B. FIGS. 18A and 18B show a vial cap 180 with the distribution holes 187, and FIG. 18A is a longitudinal cross-sectional view of the vial cap 180. As shown in FIG. 18A, the vial cap 180 includes a body 181, an intermediate member 182, and a distribution hole forming member 183, and the components described above are integrally formed into the vial cap 180. FIG. 18B is a cross-sectional view of the vial cap 180 taken along the line [B]-[B] shown in FIG. 18A, that is, a plan view of the distribution hole forming member 183. While FIGS. 18A and 18B are similar to FIGS. 17A and 17B, the vial cap 180 drawn in FIG. 18B corresponds to the vial cap 170 shown in FIG. 17B rotated clockwise 90 degrees in order to show the entire distribution holes 187 in FIG. 18A. Therefore, the total length of the distribution holes 187 are shown by the broken line and the dashed line in FIG. 18A, which corresponds to FIG. 18B. FIG. 18A only shows a discharge tube 188 and discharge hole 189 on the far side on the bottom of the vial cap 180 (upper side in FIG. 18B) because of how the cross-sectional view is produced, but does not show a lower discharge tube 188 or discharge hole 189 shown in FIG. 18B.

As shown in FIG. 18A, the vial cap 180 is formed by layering the body 181, the intermediate member 182, and the distribution hole forming member 183 to form an integrated structure. Since the configuration of the body 181 is the same as that shown in FIGS. 17A and 17B, no redundant description thereof will be made. The intermediate member 182 is a cylindrical member and has a distribution hole 185 that connects with an introduction hole 184 in the body 181. The upper surface of the intermediate member 182 is a flat surface that comes into intimate contact with the bottom surface of the body 181, and the lower surface of the intermediate member 182 is a conical surface that comes into intimate contact with a conical surface of the distribution hole forming member 183. The distribution hole forming member 183 is a cylindrical member the upper surface of which is a conical surface. The conical surface has a central portion 186 and the two arcuate distribution holes 187 (showed as grooves in FIG. 18B). The central portion 186 corresponds to the lower end of the introduction hole 185, and the arcuate distribution holes 187 extend from the central portion 186 to the outer circumferential surface of the distribution hole forming member 183. Therefore, when the lower surface of the intermediate member 182 is overlaid on the upper surface of the distribution hole forming member 183, the distribution holes 187 is formed. Each of the distribution holes 187 is a hole extending downward in an arcuate shape from the central portion 186 along the conical surface.

Therefore, the aerosol-containing gas dispensed into the introduction hole 184 in the vial cap 180 travels through the introduction hole 185 in the intermediate member 182, is split at the central portion 186, which is the apex of the conical surface of the distribution hole forming member 183, is distributed into the two arcuate distribution holes 187, and sprayed out of the openings in the outer circumferential surface of the distribution hole forming member 183 in a direction downwardly-inclined from the horizontal tangential direction along the inner circumferential surface of the collection vial (not shown). Since the thus configured vial cap 180 not only allows the aerosol-containing gas to be sprayed in a stable manner, as in the vial cap 170 shown in FIGS. 17A and 17B, but also causes the aerosol-containing gas to be sprayed out of the openings of the distribution holes 187 in a direction downwardly-inclined from the tangential direction, the liquid component unlikely accompanies the rising gas-phase $CO_2$, as compared to the vial cap 170 shown in FIGS. 17A and 17B, in which the aerosol-containing gas is sprayed in the tangential direction. Further, the speed at which the aerosol-containing gas is sprayed out of the opening of each of the distribution holes 187 is reduced to approximately half the speed in the case where an introduction tube is used, whereby the loss due to exit is reduced. The intermediate member 182 and the distribution hole forming member 183 may be integrated into a single structure.

What is claimed is:

1. A sample collection container used in a supercritical fluid system, the sample collection container comprising:
a cylindrical collection vial into which a gas containing a liquid component in the form of aerosol formed by reducing the pressure of a supercritical fluid containing a sample eluted in a separating unit to a pressure close to the atmospheric pressure is injected to collect the sample; and
a vial cap attached to an upper end opening of the collection vial,
wherein the vial cap includes a discharge hole through which the collection vial is connected to the outer air and an introduction path through which the aerosol-containing gas is externally introduced into the collection vial, wherein a distal end portion of the introduction path has an opening in the vicinity of the inner circumferential surface of the collection vial, the opening oriented in the tangential direction of the inner circumferential surface or/and in a direction downwardly-inclined from the tangential direction, wherein the aerosol-containing gas is injected under the atmospheric pressure, and wherein at least an upper portion of the vial cap is shaped into a truncated cone, and the outer circumferential surface of the upper portion is supported by the end of an upper end opening of the collection vial or a flange provided at the periphery of the vial cap is placed on the end of the upper end opening of the collection vial.

2. The sample collection container according to claim 1, wherein the introduction path is formed of an introduction hole drilled in the vial cap and an introduction tube connected to the introduction hole.

3. The sample collection container according to claim 2, wherein the introduction tube includes a straight portion connected to the introduction hole and a spiral portion following the straight portion and extending along the inner circumferential surface of the collection vial.

4. The sample collection container according to claim 3, wherein the distal end portion of the introduction tube attached to the vial cap is cut in a slanting direction.

5. A sample collection apparatus used in a supercritical fluid system in which a gas containing a liquid component in the form of aerosol formed by reducing the pressure of a supercritical fluid containing a sample eluted in a separating unit to a pressure close to the atmospheric pressure is fractionated and the gas containing the fractionated aerosol is dispensed into a sample collection container, the sample collection apparatus comprising:
  a plurality of sample collection containers of claim 3; and
  a probe that can be moved to a position above each of the collection vials, wherein the probe is lowered from the position above the collection vial and dispensing the gas containing the fractionated aerosol into the collection vial under the atmospheric pressure.

6. A sample collection method used in a supercritical fluid system in which a gas containing a liquid component in the form of aerosol is fractionated and the gas containing the fractionated aerosol is dispensed into a sample collection container, the sample collection method using a plurality of sample collection containers of claim 3 and a probe that can be moved to a position above each of the collection vials, wherein the probe is lowered from the position above the collection vial and dispensing the gas containing the fractionated aerosol into the collection vial under the atmospheric pressure, the sample collection method comprising:
  bringing a distal end portion of the probe lowered from above into fluid-leakage-free contact with the introduction path in the vial cap;
  dispensing the gas containing the fractionated aerosol through an end opening of the introduction path into the collection vial; and
  collecting the aerosol containing the sample in the collection vial and discharging the gas out of the discharge hole in the vial cap into the outer air.

7. The sample collection container according to claim 2, wherein the distal end portion of the introduction tube attached to the vial cap is cut in a slanting direction.

8. A sample collection apparatus used in a supercritical fluid system in which a gas containing a liquid component in the form of aerosol formed by reducing the pressure of a supercritical fluid containing a sample eluted in a separating unit to a pressure close to the atmospheric pressure is fractionated and the gas containing the fractionated aerosol is dispensed into a sample collection container, the sample collection apparatus comprising:
  a plurality of sample collection containers of claim 7; and
  a probe that can be moved to a position above each of the collection vials, wherein the probe is lowered from the position above the collection vial and dispensing the gas containing the fractionated aerosol into the collection vial under the atmospheric pressure.

9. A sample collection method used in a supercritical fluid system in which a gas containing a liquid component in the form of aerosol is fractionated and the gas containing the fractionated aerosol is dispensed into a sample collection container, the sample collection method using a plurality of sample collection containers of claim 7 and a probe that can be moved to a position above each of the collection vials, wherein the probe is lowered from the position above the collection vial and dispensing the gas containing the fractionated aerosol into the collection vial under the atmospheric pressure, the sample collection method comprising:
  bringing a distal end portion of the probe lowered from above into fluid-leakage-free contact with the introduction path in the vial cap;
  dispensing the gas containing the fractionated aerosol through an end opening of the introduction path into the collection vial; and
  collecting the aerosol containing the sample in the collection vial and discharging the gas out of the discharge hole in the vial cap into the outer air.

10. A sample collection apparatus used in a supercritical fluid system in which a gas containing a liquid component in the form of aerosol formed by reducing the pressure of a supercritical fluid containing a sample eluted in a separating unit to a pressure close to the atmospheric pressure is fractionated and the gas containing the fractionated aerosol is dispensed into a sample collection container, the sample collection apparatus comprising:
  a plurality of sample collection containers of claim 2; and
  a probe that can be moved to a position above each of the collection vials, wherein the probe is lowered from the position above the collection vial and dispensing the gas containing the fractionated aerosol into the collection vial under the atmospheric pressure.

11. A sample collection method used in a supercritical fluid system in which a gas containing a liquid component in the form of aerosol is fractionated and the gas containing the fractionated aerosol is dispensed into a sample collection container, the sample collection method using a plurality of sample collection containers of claim 2 and a probe that can be moved to a position above each of the collection vials, wherein the probe is lowered from the position above the collection vial and dispensing the gas containing the fractionated aerosol into the collection vial under the atmospheric pressure, the sample collection method comprising:
  bringing a distal end portion of the probe lowered from above into fluid-leakage-free contact with the introduction path in the vial cap;
  dispensing the gas containing the fractionated aerosol through an end opening of the introduction path into the collection vial; and
  collecting the aerosol containing the sample in the collection vial and discharging the gas out of the discharge hole in the vial cap into the outer air.

12. The sample collection container according to claim 1, wherein the introduction path is formed of an introduction hole vertically drilled in the vial cap, a introduction hole drilled in a cylindrical extension extending from the vial cap into the collection vial, and a plurality of distribution holes extending from the introduction hole to the outer circumferential surface of the extension, each of the distribution holes having an opening at the outer circumferential surface.

13. The sample collection container according to claim 12, wherein each of the distribution holes has an arcuate shape, and horizontally extends from the lower end of the introduction hole or is inclined downward along a conical surface whose apex coincides with the lower end of the introduction hole.

14. A sample collection apparatus used in a supercritical fluid system in which a gas containing a liquid component in the form of aerosol formed by reducing the pressure of a supercritical fluid containing a sample eluted in a separating unit to a pressure close to the atmospheric pressure is fractionated and the gas containing the fractionated aerosol is dispensed into a sample collection container, the sample collection apparatus comprising:
  a plurality of sample collection containers of claim 13; and
  a probe that can be moved to a position above each of the collection vials, wherein the probe is lowered from the position above the collection vial and dispensing the gas containing the fractionated aerosol into the collection vial under the atmospheric pressure.

15. A sample collection apparatus used in a supercritical fluid system in which a gas containing a liquid component in the form of aerosol formed by reducing the pressure of a supercritical fluid containing a sample eluted in a separating unit to a pressure close to the atmospheric pressure is fractionated and the gas containing the fractionated aerosol is dispensed into a sample collection container, the sample collection apparatus comprising:
  a plurality of sample collection containers of claim 12; and
  a probe that can be moved to a position above each of the collection vials, wherein the probe is lowered from the position above the collection vial and dispensing the gas containing the fractionated aerosol into the collection vial under the atmospheric pressure.

16. A sample collection method used in a supercritical fluid system in which a gas containing a liquid component in the form of aerosol is fractionated and the gas containing the fractionated aerosol is dispensed into a sample collection container, the sample collection method using a plurality of sample collection containers of claim 12 and a probe that can be moved to a position above each of the collection vials, wherein the probe is lowered from the position above the collection vial and dispensing the gas containing the fractionated aerosol into the collection vial under the atmospheric pressure, the sample collection method comprising:
  bringing a distal end portion of the probe lowered from above into fluid-leakage-free contact with the introduction path in the vial cap;
  dispensing the gas containing the fractionated aerosol through an end opening of the introduction path into the collection vial; and
  collecting the aerosol containing the sample in the collection vial and discharging the gas out of the discharge hole in the vial cap into the outer air.

17. A sample collection apparatus used in a supercritical fluid system in which a gas containing a liquid component in the form of aerosol formed by reducing the pressure of a supercritical fluid containing a sample eluted in a separating unit to a pressure close to the atmospheric pressure is fractionated and the gas containing the fractionated aerosol is dispensed into a sample collection container, the sample collection apparatus comprising:
  a plurality of sample collection containers of claim 1; and
  a probe that can be moved to a position above each of the collection vials, wherein the probe is lowered from the position above the collection vial and dispensing the gas containing the fractionated aerosol into the collection vial under the atmospheric pressure.

18. A sample collection method used in a supercritical fluid system in which a gas containing a liquid component in the form of aerosol is fractionated and the gas containing the fractionated aerosol is dispensed into a sample collection container, the sample collection method using a plurality of sample collection containers of claim 1 and a probe that can be moved to a position above each of the collection vials, wherein the probe is lowered from the position above the collection vial and dispensing the gas containing the fractionated aerosol into the collection vial under the atmospheric pressure, the sample collection method comprising:
  bringing a distal end portion of the probe lowered from above into fluid-leakage-free contact with the introduction path in the vial cap;
  dispensing the gas containing the fractionated aerosol through an end opening of the introduction path into the collection vial; and
  collecting the aerosol containing the sample in the collection vial and discharging the gas out of the discharge hole in the vial cap into the outer air.

* * * * *